(12) United States Patent
Laaksonen et al.

(10) Patent No.: US 10,984,902 B2
(45) Date of Patent: Apr. 20, 2021

(54) METHODS AND SYSTEMS FOR ADAPTIVE RADIOTHERAPY TREATMENT PLANNING USING DEEP LEARNING ENGINES

(71) Applicant: Varian Medical Systems International AG, Palo Alto, CA (US)

(72) Inventors: Hannu Laaksonen, Espoo (FI); Janne Nord, Espoo (FI); Sami Petri Perttu, Helsinki (FI)

(73) Assignee: VARIAN MEDICAL SYSTEMS INTERNATIONAL AG

( * ) Notice: Subject to any disclaimer, the term of this patent is extended or adjusted under 35 U.S.C. 154(b) by 220 days.

(21) Appl. No.: 16/145,606

(22) Filed: Sep. 28, 2018

(65) Prior Publication Data
US 2020/0105394 A1 Apr. 2, 2020

(51) Int. Cl.
| | |
|---|---|
| *G06N 3/08* | (2006.01) |
| *G16H 20/40* | (2018.01) |
| *A61N 5/10* | (2006.01) |
| *G16H 30/40* | (2018.01) |
| *G16B 40/00* | (2019.01) |

(52) U.S. Cl.
CPC .......... *G16H 20/40* (2018.01); *A61N 5/1031* (2013.01); *A61N 5/1038* (2013.01); *A61N 5/1039* (2013.01); *G06N 3/08* (2013.01); *G16B 40/00* (2019.02); *G16H 30/40* (2018.01); *A61N 2005/1041* (2013.01)

(58) Field of Classification Search
CPC combination set(s) only.
See application file for complete search history.

(56) References Cited

U.S. PATENT DOCUMENTS

| | | |
|---|---|---|
| 10,342,994 B2 | 7/2019 | Kuusela et al. |
| 10,346,593 B2 | 7/2019 | Kuusela et al. |
| (Continued) | | |

FOREIGN PATENT DOCUMENTS

| | | |
|---|---|---|
| WO | 2018048575 A1 | 3/2018 |

OTHER PUBLICATIONS

Konstantinos Kamnitsas et al., "Efficient Multi-Scale 3D CNN with Fully Connected CRF for Accurate Brain Lesion Segmentation", Medical Image Analysis, Feb. 2017, pp. 61-78, vol. 36, Elsevier B.V.

(Continued)

*Primary Examiner* — Iman K Kholdebarin
(74) *Attorney, Agent, or Firm* — SU IP Consulting

(57) ABSTRACT

Example methods for adaptive radiotherapy treatment planning using deep learning engines are provided. One example method may comprise obtaining treatment image data associated with a first imaging modality. The treatment image data may be acquired during a treatment phase of a patient. Also, planning image data associated with a second imaging modality may be acquired prior to the treatment phase to generate a treatment plan for the patient. The method may also comprise: in response to determination that an update of the treatment plan is required, transforming the treatment image data associated with the first imaging modality to generate transformed image data associated with the second imaging modality. The method may further comprise: processing, using the deep learning engine, the transformed image data to generate output data for updating the treatment plan.

18 Claims, 10 Drawing Sheets

(56) References Cited

U.S. PATENT DOCUMENTS

| | | | |
|---|---|---|---|
| 2013/0085343 A1 | 4/2013 | Toimela et al. | |
| 2014/0171726 A1* | 6/2014 | Gum | A61N 5/1049 |
| | | | 600/1 |
| 2015/0094519 A1 | 4/2015 | Kuusela et al. | |
| 2015/0360056 A1* | 12/2015 | Xing | A61N 5/1075 |
| | | | 600/1 |
| 2016/0129282 A1 | 5/2016 | Yin et al. | |
| 2016/0140300 A1 | 5/2016 | Purdie et al. | |
| 2017/0177812 A1* | 6/2017 | Sjolund | G16H 50/20 |
| 2018/0043182 A1 | 2/2018 | Wu et al. | |
| 2019/0220986 A1* | 7/2019 | Magro | G06T 7/38 |
| 2019/0232087 A1 | 8/2019 | Cordero Marcos et al. | |
| 2019/0328348 A1 | 10/2019 | De Man et al. | |
| 2019/0329072 A1* | 10/2019 | Magro | G01T 1/02 |
| 2019/0333623 A1* | 10/2019 | Hibbard | G16H 20/40 |
| 2020/0104695 A1* | 4/2020 | Laaksonen | A61N 5/1031 |
| 2020/0105394 A1* | 4/2020 | Laaksonen | A61N 5/1038 |
| 2020/0105399 A1* | 4/2020 | Laaksonen | G06N 3/08 |
| 2020/0197726 A1 | 6/2020 | Cordero Marcos et al. | |

OTHER PUBLICATIONS

Olaf Ronneberger et al., "U-Net: Convolutional Networks for Biomedical Image Segmentation", Computer Science Department and BIOSS Centre for Biological Signalling Studies, May 18, 2015.

Extended European Search Report, European application No. 19199019.1, dated Feb. 19, 2020.

C Kontaxis et al., "Towards Fast Online Intrafraction Replanning for Free-breathing Stereotactic Body Radiation Therapy with the MR-linac", Physics in Medicine & Biology, 2017, pp. 7233-7248, vol. 62.

A. Hunt et al., "Adaptive Radiotherapy Enabled by MRI Guidance", Clinial Oncology, 2018, pp. 711-719, vol. 30.

* cited by examiner

TRAINING PHASE 401

INFERENCE PHASE 402

TRAINING PHASE 701

INFERENCE PHASE 702

METHODS AND SYSTEMS FOR ADAPTIVE RADIOTHERAPY TREATMENT PLANNING USING DEEP LEARNING ENGINES

CROSS-REFERENCE TO RELATED APPLICATIONS

This application is related in subject matter to U.S. patent applications Ser. Nos. 16/145,461 and 16/145,673. The U.S. patent applications, including any appendices or attachments thereof, are incorporated by reference herein in its entirety.

BACKGROUND

Unless otherwise indicated herein, the approaches described in this section are not prior art to the claims in this application and are not admitted to be prior art by inclusion in this section.

Radiotherapy is an important part of a treatment for reducing or eliminating unwanted tumors from patients. Unfortunately, applied radiation does not inherently discriminate between an unwanted tumor and any proximal healthy structures such as organs, etc. This necessitates careful administration to restrict the radiation to the tumor (i.e., target). Ideally, the goal is to deliver a lethal or curative radiation dose to the tumor, while maintaining an acceptable dose level in the proximal healthy structures. However, to achieve this goal, conventional radiotherapy treatment planning and/or adaptive radiotherapy treatment planning may be time and labor intensive.

SUMMARY

According to a first aspect of the present disclosure, example methods and systems for radiotherapy treatment planning using a deep learning engine are provided. Various examples will be discussed using FIG. 1 to FIG. 5. The deep learning engine may include at least a first processing pathway, a second processing pathway and a third processing pathway. One example method may comprise obtaining first image data associated with a patient; generating first feature data by processing the first image data associated with a first resolution level using the first processing pathway; generating second feature data by processing second image data associated with a second resolution level using the second processing pathway; and generating third feature data by processing third image data associated with a third resolution level using the third processing pathway. The example method may also comprise generating a first combined set of feature data associated with the second resolution level based on the second feature data and the third feature data, and a second combined set of feature data associated with the first resolution level based on the first feature data and the first combined set. Further, the example method may comprise generating output data associated with radiotherapy treatment of the patient. For example, the output data may include at least one of the following: structure data associated with the patient, dose data associated with the patient, and treatment delivery data for a treatment delivery system.

According to a second aspect of the present disclosure, example methods and systems for adaptive radiotherapy treatment planning using a deep learning engine are provided. Various examples will be discussed using FIG. 6 and FIG. 7. One example method may comprise obtaining treatment image data associated with a first imaging modality. The treatment image data may be acquired during a treatment phase of a patient. Also, planning image data associated with a second imaging modality may be acquired prior to the treatment phase to generate a treatment plan for the patient. The method may also comprise: in response to determination that an update of the treatment plan is required, transforming the treatment image data associated with the first imaging modality to generate transformed image data associated with the second imaging modality. The method may further comprise: processing, using the deep learning engine, the transformed image data to generate output data for updating the treatment plan. For example, the output data may be at least one of the following: structure data associated with the patient, dose data associated with the patient, and treatment delivery data for a treatment delivery system.

According to a third aspect of the present disclosure, example methods and systems for adaptive radiotherapy treatment planning using a deep learning engine are provided. Various examples will be discussed using FIG. 6 and FIG. 8. One example method may comprise obtaining treatment image data associated with a first imaging modality and planning image data associated with a second imaging modality. The planning image data may be acquired prior to the treatment phase to generate a treatment plan for the patient. The method may also comprise: in response to determination that an update of the treatment plan is required, processing, using the deep learning engine, the treatment image data and the planning image data to generate output data for updating the treatment plan. For example, the output data may be at least one of the following: structure data associated with the patient, dose data associated with the patient, and treatment delivery data for a treatment delivery system.

DETAILED DESCRIPTION

The technical details set forth in the following description enable a person skilled in the art to implement one or more embodiments of the present disclosure.

Figure 1:
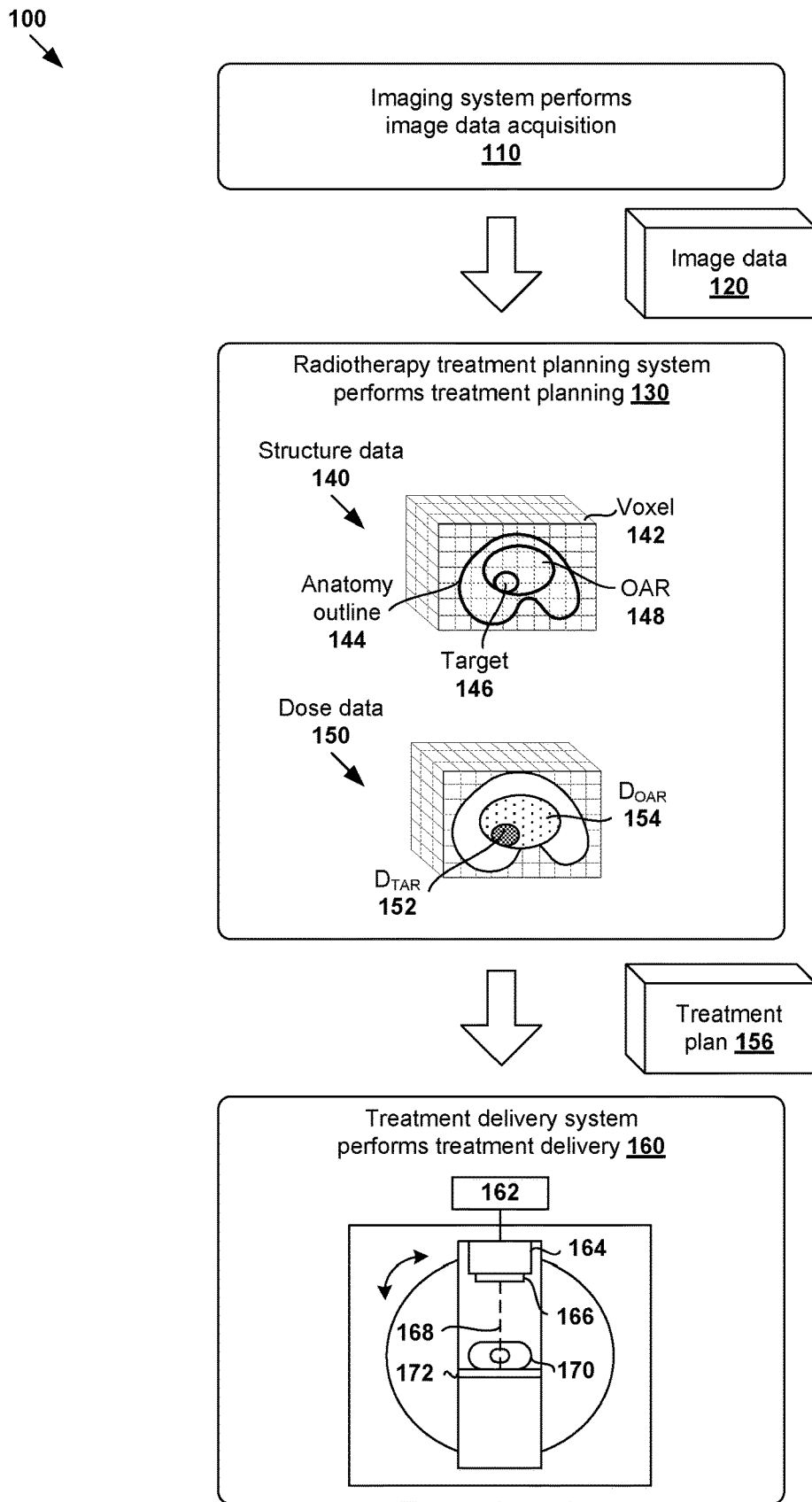
FIG. 1 is a schematic diagram illustrating an example process flow for radiotherapy treatment.

FIG. 1 is a schematic diagram illustrating example process flow 100 for radiotherapy treatment. Example process 100 may include one or more operations, functions, or actions illustrated by one or more blocks. The various blocks may be combined into fewer blocks, divided into additional blocks, and/or eliminated based upon the desired implementation. In the example in FIG. 1, radiotherapy treatment generally includes various stages, such as an imaging system performing image data acquisition for a patient (see 110); a radiotherapy treatment planning system (see 130) generating a suitable treatment plan (see 156) for the patient; and a treatment delivery system (see 160) delivering treatment according to the treatment plan.

In more detail, at 110 in FIG. 1, image data acquisition may be performed using an imaging system to capture image data 120 associated with a patient (particularly the patient's anatomy). Any suitable medical image modality or modalities may be used, such as computed tomography (CT), cone beam computed tomography (CBCT), positron emission tomography (PET), magnetic resonance imaging (MRI), single photon emission computed tomography (SPECT), any combination thereof, etc. For example, when CT or MRI is used, image data 120 may include a series of two-dimensional (2D) images or slices, each representing a cross-sectional view of the patient's anatomy, or may include volumetric or three-dimensional (3D) images of the patient, or may include a time series of 2D or 3D images of the patient (e.g., four-dimensional (4D) CT or 4D CBCT).

At 130 in FIG. 1, radiotherapy treatment planning may be performed during a planning phase to generate treatment plan 156 based on image data 120. Any suitable number of treatment planning tasks or steps may be performed, such as segmentation, dose prediction, projection data prediction, treatment plan generation, etc. For example, segmentation may be performed to generate structure data 140 identifying various segments or structures may from image data 120. In practice, a three-dimensional (3D) volume of the patient's anatomy may be reconstructed from image data 120. The 3D volume that will be subjected to radiation is known as a treatment or irradiated volume that may be divided into multiple smaller volume-pixels (voxels) 142. Each voxel 142 represents a 3D element associated with location (i, j, k) within the treatment volume. Structure data 140 may be include any suitable data relating to the contour, shape, size and location of patient's anatomy 144, target 146 and any organ-at-risk (OAR) 148.

In another example, dose prediction may be performed to generate dose data 150 specifying radiation dose to be delivered to target 146 (denoted "$D_{TAR}$" at 152) and radiation dose for OAR 148 (denoted "$D_{OAR}$" at 154). In practice, target 146 may represent a malignant tumor (e.g., prostate tumor, etc.) requiring radiotherapy treatment, and OAR 148 a proximal healthy structure or non-target structure (e.g., rectum, bladder, etc.) that might be adversely affected by the treatment. Target 146 is also known as a planning target volume (PTV). Although an example is shown in FIG. 1, the treatment volume may include multiple targets 146 and OARs 148 with complex shapes and sizes. Further, although shown as having a regular shape (e.g., cube), voxel 142 may have any suitable shape (e.g., non-regular). Depending on the desired implementation, radiotherapy treatment planning at block 130 may be performed based on any additional and/or alternative data, such as prescription, disease staging, biologic or radiomic data, genetic data, assay data, biopsy data, past treatment or medical history, any combination thereof, etc.

Based on structure data 140 and dose data 150, treatment plan 156 may be generated include 2D fluence map data for a set of beam orientations or angles. Each fluence map specifies the intensity and shape (e.g., as determined by a multileaf collimator (MLC)) of a radiation beam emitted from a radiation source at a particular beam orientation and at a particular time. For example, in practice, intensity modulated radiotherapy treatment (IMRT) or any other treatment technique(s) may involve varying the shape and intensity of the radiation beam while at a constant gantry and couch angle. Alternatively or additionally, treatment plan 156 may include machine control point data (e.g., jaw and leaf positions), volumetric modulated arc therapy (VMAT) trajectory data for controlling a treatment delivery system, etc. In practice, block 130 may be performed based on goal doses prescribed by a clinician (e.g., oncologist, dosimetrist, planner, etc.), such as based on the clinician's experience, the type and extent of the tumor, patient geometry and condition, etc.

At 160 in FIG. 1, treatment delivery is performed during a treatment phase to deliver radiation to the patient according to treatment plan 156. For example, radiotherapy treatment delivery system 160 may include rotatable gantry 164 to which radiation source 166 is attached. During treatment delivery, gantry 164 is rotated around patient 170 supported on structure 172 (e.g., table) to emit radiation beam 168 at various beam orientations according to treatment plan 156. Controller 162 may be used to retrieve treatment plan 156 and control gantry 164, radiation source 166 and radiation beam 168 to deliver radiotherapy treatment according to treatment plan 156.

It should be understood that any suitable radiotherapy treatment delivery system(s) may be used, such as mechanic-arm-based systems, tomotherapy type systems, brachy, sirex spheres, any combination thereof, etc. Additionally, examples of the present disclosure may be applicable to particle delivery systems (e.g., proton, carbon ion, etc.). Such systems may employ either a scattered particle beam that is then shaped by a device akin to an MLC, or may instead employ a scanning beam of adjustable energy, spot size, and dwell time.

Conventionally, radiotherapy treatment planning at block 130 in FIG. 1 is time and labor intensive. For example, it usually requires a team of highly skilled and trained oncologists and dosimetrists to manually delineate structures of interest by drawing contours or segmentations on image data 120. These structures are manually reviewed by a physician, possibly requiring adjustment or re-drawing. In many cases, the segmentation of critical organs can be the most time-consuming part of radiation treatment planning. After the structures are agreed upon, there are additional labor-intensive steps to process the structures to generate a clinically-optimal treatment plan specifying treatment delivery data such as beam orientations and trajectories, as well as corresponding 2D fluence maps. These steps are often complicated by a lack of consensus among different physicians and/or clinical sites as to what constitutes "good" contours or segmentation. In practice, there might be a huge variation in the way structures or segments are drawn by different clinical experts. The variation may result in uncertainty in target volume size and shape, as well as the exact proximity, size and shape of OARs that should receive minimal radiation dose. Even for a particular clinical expert, there might be variation in the way segments are drawn on different days.

According to examples of the present disclosure, artificial intelligence (AI) techniques may be applied to ameliorate various challenges associated with radiotherapy treatment planning. In particular, deep learning engine(s) may be used to automate radiotherapy treatment planning step(s) and/or adaptive radiotherapy treatment planning step(s). Examples of the present disclosure may be implemented to improve the efficiency of radiotherapy treatment planning and possibly the treatment outcome, such as increasing the tumor control probability and/or reducing the likelihood of health complications or death due to radiation overdose in the healthy structures. For example, automatic segmentation of image data 120 would be of great benefit in speeding up the workflow and enabling various applications, such automatic treatment planning and radiotherapy treatment adaptation.

Throughout the present disclosure, the term "deep learning" may refer generally to a class of approaches that utilizes many layers or stages of nonlinear data processing for feature learning as well as pattern analysis and/or classification. Accordingly, the term "deep learning model" may refer to a hierarchy of layers of nonlinear data processing that include an input layer, an output layer, and multiple (i.e., two or more) "hidden" layers between the input and output layers. These layers may be trained from end-to-end (e.g., from the input layer to the output layer) to extract feature(s) from an input and classify the feature(s) to produce an output (e.g., classification label or class).

Accordingly, the term "deep learning engine" may refer to any suitable hardware and/or software component(s) of a computer system that are capable of executing algorithms according to any suitable deep learning model(s). Depending on the desired implementation, any suitable deep learning model(s) may be used, such as convolutional neural network, recurrent neural network, deep belief network, or any combination thereof, etc. In practice, a neural network is generally formed using a network of processing elements (called "neurons," "nodes," etc.) that are interconnected via connections (called "synapses," "weights," etc.).

Deep learning approaches should be contrasted against machine learning approaches that have been applied to, for example, automatic segmentation. In general, these approaches involve extracting (hand-designed) feature vectors from images, such as for every voxel, etc. Then, the feature vectors may be used as input to a machine learning model that classifies which class each voxel belongs to. However, such machine learning approaches usually do not make use of complete image data and additional constraints may be required. Another challenge is that these approaches rely on a high dimension of hand-designed features in order to accurately predict the class label for each voxel. Solving a high-dimensional classification problem is computationally expensive and requires a large amount of memory. Some approaches use lower dimensional features (e.g., using dimensionality reduction techniques) but they may decrease the prediction accuracy.

In the following, various examples will be discussed below using FIG. 1 to FIG. 10. In particular, radiotherapy treatment planning using deep learning engine(s) will be discussed using FIG. 1 to FIG. 5. Further, adaptive radiotherapy treatment planning using deep learning engine(s) will be discussed using FIG. 6 to FIG. 9. Examples of the present disclosure may be implemented using any suitable computer system(s), an example of which is shown in FIG. 10.

Deep Learning Engine with Multiple Processing Pathways

Figure 2:
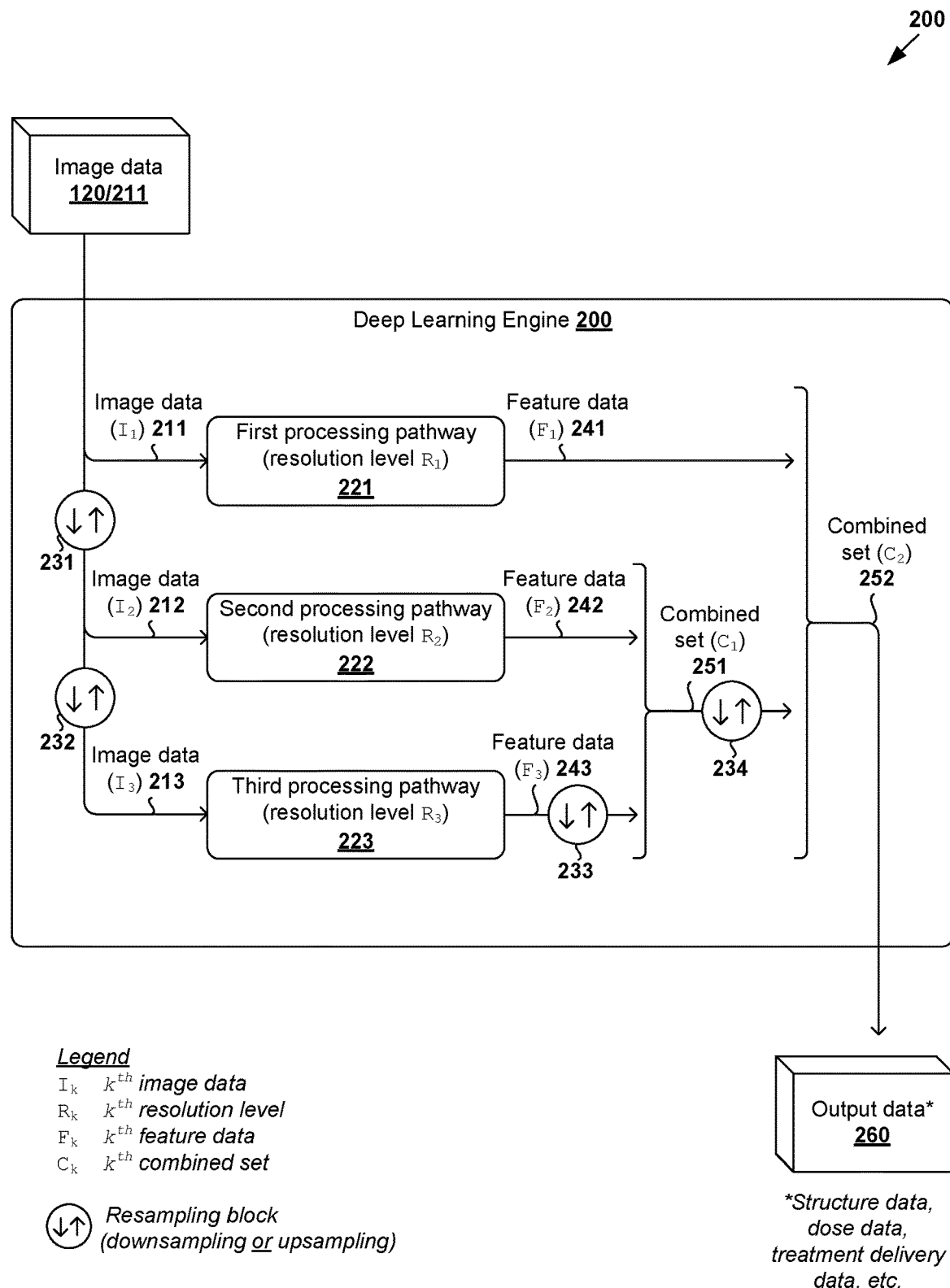
FIG. 2 is a schematic diagram illustrating an example deep learning engine with multiple processing pathways to perform radiotherapy treatment planning.
Figure 3:
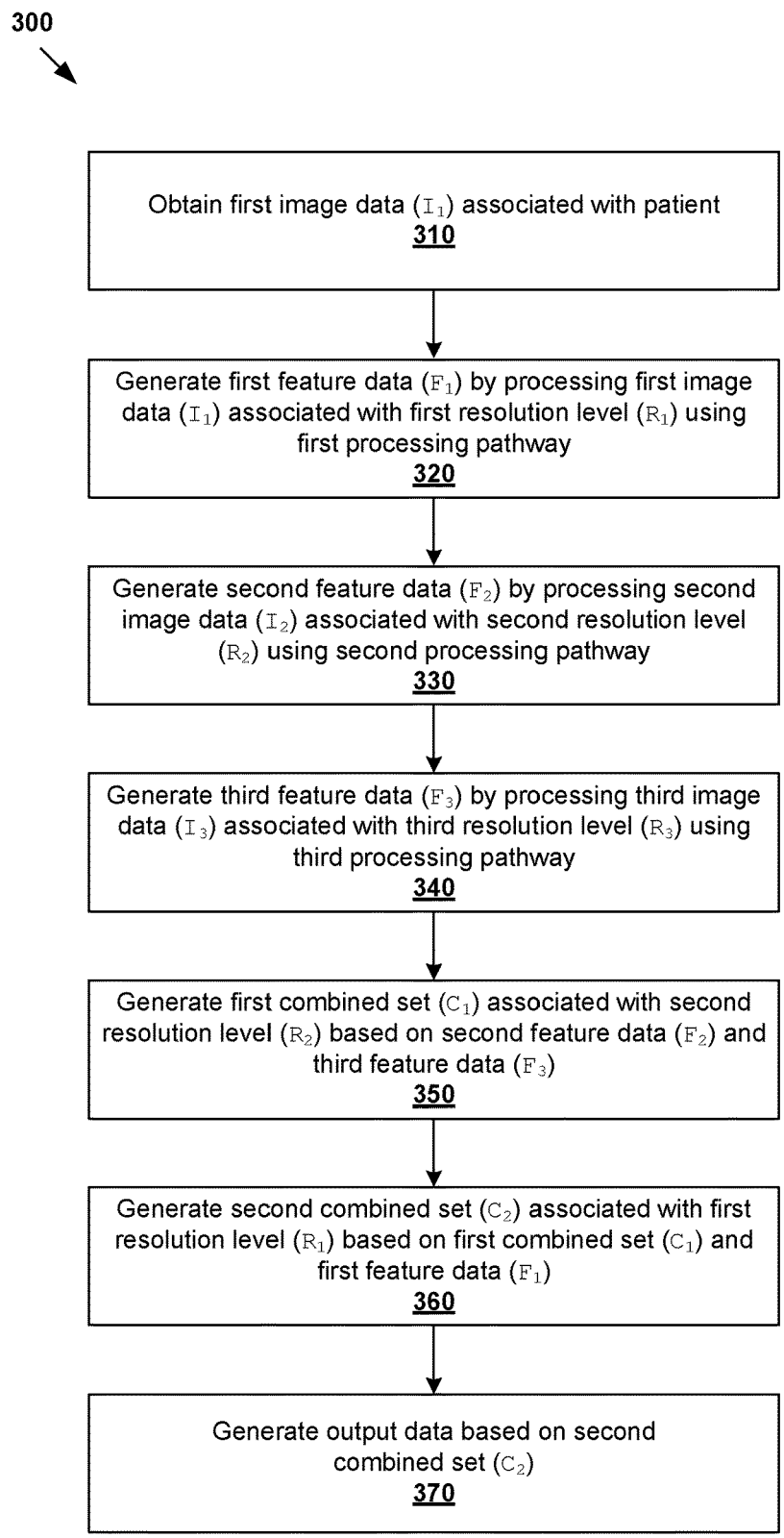
FIG. 3 is a flowchart of an example process for a computer system to perform radiotherapy treatment planning using a deep learning engine.

According to a first aspect of the present disclosure, radiotherapy treatment planning may be improved using a deep learning engine with multiple (K) processing pathways to process medical image data at different resolution levels. Some examples will be explained using FIG. 2 and FIG. 3. In particular, FIG. 2 is a schematic diagram illustrating example deep learning engine 200 with multiple processing pathways for radiotherapy treatment planning. FIG. 3 is a flowchart of example process 300 for a computer system to perform radiotherapy treatment planning using deep learning engine 200. Example process 300 may include one or more operations, functions, or actions illustrated by one or more blocks, such as 310 to 370. The various blocks may be combined into fewer blocks, divided into additional blocks, and/or eliminated based upon the desired implementation.

In the example in FIG. 2, multi-resolution deep learning engine 200 includes at least three (K=3) processing pathways 221-223 to process respective image data 211-213 at different resolution levels (denoted as $R_k=R_1, R_2, R_3$) to generate output data 260. Image data 211-213 of multiple resolution levels may be fed separately into specifically-tailored processing pathways 221-223. This way, deep learning engine 200 may achieve a larger receptive field to improve of prediction outcome compared to conventional approaches that rely on a single processing pathway. In particular, to achieve the same (i.e., larger) receptive field, a single-pathway deep learning engine would have to be deeper (e.g., more layers) and therefore require more computing power.

In practice, a larger receptive field is better than a smaller one to facilitate extraction and analysis of both local and global feature data in image data 211-213 to produce better quality output data. In general, deep neural networks may be difficult to tune to work properly for medical image data, as the needed accuracy and reliability is relatively high. By breaking the image processing problem into multiple resolution levels, examples of the present disclosure may be implemented in a resource-efficient manner. At a user's site with limited processing resources, for example, memory-efficient approaches are preferred to improve efficiency. For example, the processing cost is lower at a lower resolution in the sense that a processing pathway may process more distant data (e.g., feature data at different physical distances) at the same cost compared to the case where there is no downsampling.

Referring also to FIG. 3, at 310, first image data 120/211 associated with a patient is obtained. Here, the term "obtain" may refer generally to a computer system accessing or retrieving image data 120/211 from any suitable source (e.g., another computer system), memory or storage (e.g., local or remote), etc. In practice, first image data 211 may be 2D or 3D image data acquired using any suitable imaging modality or modalities.

At 320 in FIG. 3, first image data ($I_1$) 211 associated with a first resolution level ($R_1$) is processed using first processing pathway 221 to generate first feature data ($F_1$) 241. At 330 in FIG. 3, second image data ($I_2$) 212 associated with a second resolution level ($R_2$) is processed using second processing pathway 222 to generate second feature data ($F_2$) 242. At 340 in FIG. 3, third image data ($I_3$) 213 associated with a third resolution level ($R_3$) is processed using third processing pathway 223 to generate third feature data ($F_3$) 243. In practice, a "processing pathway" may be implemented using any suitable architecture, such as convolutional block(s) or layer(s) to generate feature data.

At 350 in FIG. 3, first combined set of feature data ($C_1$) 251 associated with the second resolution level ($R_2$) is generated based on second feature data ($F_2$) 242 and third feature data ($F_3$) 243. At 360 in FIG. 3, second combined set of feature data ($C_2$) 252 associated with the first resolution level ($R_1$) is generated based on first combined set ($C_1$) 251 and first feature data ($F_1$) 241. At 370 in FIG. 3, output data 260 associated with radiotherapy treatment of the patient is generated based on second combined set ($C_2$) 252. Examples of the present disclosure may be implemented to facilitate better integration of feature data 241-243 of different resolution levels from respective processing pathways 221-223.

Depending on the desired implementation, deep learning engine 200 may be trained to perform automatic segmentation to generate output data=structure data (e.g., 140 in FIG. 1), dose prediction to generate output=dose data (e.g., 150 in FIG. 1), treatment delivery data estimation to generate output=treatment delivery data, or any combination thereof. For example, in the case of automatic segmentation, the structure data may include segmented and labeled images specifying the contour, shape, size and/or location of structure(s) or segment(s) that are identifiable from image data 120/211, such as patient's anatomy 144, target 146, and OAR 148 in FIG. 1. In the case of dose prediction, the dose data may specify radiation dose for target 146 and OAR 148 (see also 152-154 in FIG. 1). In the case of treatment delivery data estimation, the "treatment delivery data" may be structure projection data (e.g., beam trajectories and/or orientations), fluence map data, etc.

In the example in FIG. 2, second image data ($I_2$) 212 may be generated based on first image data ($I_1$) 211, and third image data ($I_3$) 213 based on second image data ($I_2$) 212 or first image data ($I_1$) 211. Deep learning engine 200 includes matching resampling (i.e., downsampling or upsampling) blocks 231-234. For example, in the case of $R_1>R_2>R_3$ (to be discussed using FIG. 4 and FIG. 5), downsampling blocks 231-232 may be used to reduce the resolution level, and matching upsampling blocks 233-234 to increase the resolution level.

In the following, examples relating to automatic segmentation will be described using FIG. 4 and dose prediction using FIG. 5. Although exemplified using deep convolutional neural networks, it should be understood that any alternative and/or additional deep learning model(s) may be used to implement deep learning engine 200/400/500 according to examples of the present disclosure.

Automatic Segmentation

Figure 4:
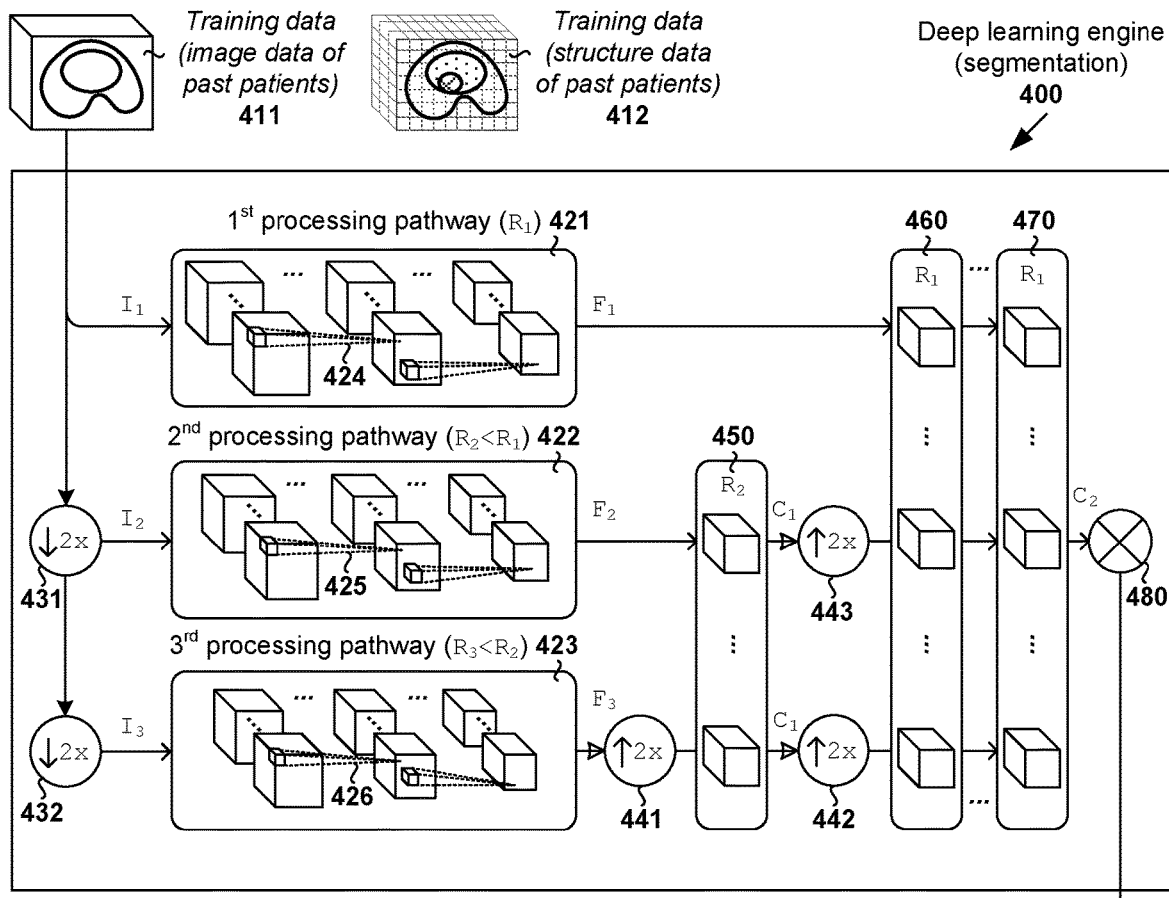
FIG. 4 is a schematic diagram illustrating an example deep learning engine to perform automatic segmentation of image data for radiotherapy treatment planning.
Figure 4:
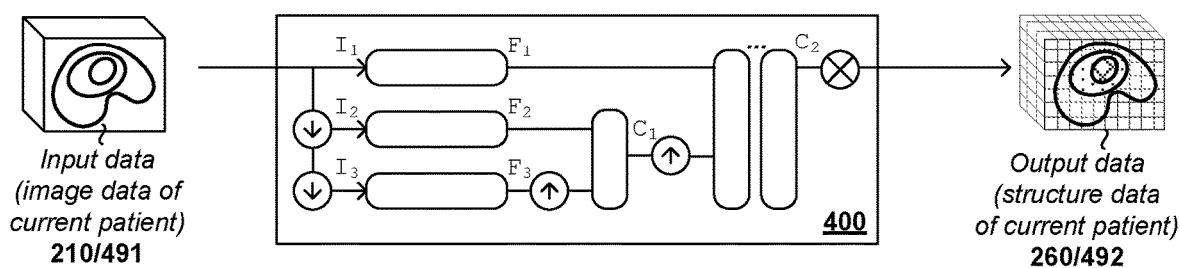

FIG. 4 is a schematic diagram illustrating example deep learning engine 400 to perform automatic segmentation of image data for radiotherapy treatment planning. Similar to the example in FIG. 2, deep learning engine 400 includes K=3 processing pathways (see 421-423) that are trained during training phase 401. Once trained, deep learning engine 400 may be used (e.g., by a clinician) to perform automatic segmentation for actual patients during inference phase 402.

(a) Training Data

During training phase 401, deep learning engine 400 may be trained using any suitable training data 411-412 relating to automatic segmentation. In practice, training data 411-412 may include example input data=unsegmented image data 411, and example output data=structure data 412 (also known as segmentation data). Structure data 412 may identify any suitable contour, shape, size and/or location of structure(s) or segment(s) of a patient's anatomy, such as target(s), OAR(s), etc. Image data 411 may include 2D or 3D images of the patient's anatomy, and captured using any suitable imaging modality or modalities. Depending on the desired implementation, structure data 412 may be manually generated and clinically validated by trained professionals using any suitable approach.

The aim of training phase 401 is to train deep learning engine 400 to perform automatic segmentation by mapping input data=image data 411 to example output data=structure data 412. Training phase 401 may involve finding weights that minimize the training error between training structure data 412, and estimated structure data 482 generated by deep learning engine 400. In practice, deep learning engine 200 may be trained identify multiple targets and OARs of any suitable shapes and sizes.

For example, in relation to prostate cancer, image data 411 may include image data of a patient's prostate. In this case, structure data 412 may identify a target representing the patient's prostate, and an OAR representing a proximal healthy structure such as rectum or bladder. In relation to lung cancer treatment, image data 411 may include image data of a patient's lung. In this case, structure data 412 may identify a target representing cancerous lung tissue, and an OAR representing proximal healthy lung tissue, esophagus, heart, etc. In relation to brain cancer, image data 411 may include image data of a patient's brain, in which case structure data 412 may identify a target representing a brain tumor, and an OAR representing a proximal optic nerve, brain stem, etc.

In practice, training data 411-412 may be user-generated through observations and experience to facilitate supervised learning. For example, training data 411-412 may be extracted from past treatment plans developed for past patients. Training data 411-412 may be pre-processed using any suitable data augmentation approach (e.g., rotation, flipping, translation, scaling, noise addition, cropping, any combination thereof, etc.) to produce a new dataset with modified properties to improve model generalization using ground truth. In practice, a 3D volume of the patient that will be subjected to radiation is known as a treatment volume, which may be divided into multiple smaller volume-pixels (voxels). In this case, structure data 412 may specify a class label (e.g., "target," "OAR," etc.) associated with each voxel in the 3D volume. Depending on the desired implementation, structure data 412 may identify multiple targets and OARs of any suitable shapes and sizes.

(b) Processing Pathways and Layers

Deep learning engine 400 includes three processing pathways 421-423 (k=1, 2, 3) to process image data at different resolution levels ($R_k=R_1, R_2, R_3$). First processing pathway 421 (k=1) is configured to process first image data ($I_1$) at a first resolution level $R_1$ (e.g., 1×). Second processing pathway 422 (k=2) is configured to process second image data ($I_2$) at a second resolution level $R_2<R_1$ to enlarge the receptive field. Third processing pathway 423 (k=3) is configured to process third image data ($I_3$) at a third resolution level $R_3<R_2<R_1$ to further enlarge the receptive field.

In the example in FIG. 4, the input to first processing pathway 421 is image data 411. The input to second processing pathway 422 is image data 411 that has been downsampled (e.g., by a factor of 2×) by downsampling block 431. The input to the third processing pathway 423 is image data 411 that has been downsampled by both downsampling blocks 431-432 (e.g., by a total factor of 4×). Downsampling blocks 431-432 have matching upsampling blocks 441-443 for upsampling before feature data (see $F_1$, $F_2$, $F_3$) from respective processing pathways 421-423 are combined. In other words, each downsampling step has a corresponding (i.e., matching) upsampling step to readjust the resolution level. Downsampling blocks 431-432 may be implemented using subsampling, pooling, etc., and upsampling blocks 441-443 using transposed convolutions, repeating, etc.

By processing image data 411 at multiple resolution levels, processing pathways 421-423 provide different views into image data 411 to achieve a larger receptive field. In practice, medical image data generally includes both local and global feature data of a patient's anatomy, where the terms "local" and "global" are relative in nature. For example, the local feature data may provide a microscopic view of the patient's anatomy, such as tissue texture, whether a structure has a limiting border, etc. In contrast, the global feature data may provide a relatively macroscopic view of the patient's anatomy, such as which region the anatomy is located (e.g., pelvis, abdomen, head and neck, etc.), orientation (e.g., to the left, to the right, front, back), etc.

In the example in FIG. 4, first processing pathway 421 may process image data 411 at the highest resolution level ($R_1$) to analyze local tissue texture. Second processing pathway 422 may process image data 411 at an intermediate resolution level ($R_2<R_1$) to analyze tissue type changes for evidence of nearby structural boundaries. Third processing pathway 422 may process image data 411 at the coarsest resolution level ($R_3<R_2<R_1$) to analyze landmarks such as bones and body outline. Processing image data 411 at a lower resolution level generally requires less processing. This is especially significant for 3D image data processing, where halving the resolution may cut the processing cost to ⅛. This allows more resources to be devoted to more accurate segmentation, such as more channels in processing pathways 421-423.

Using deep convolutional neural networks for example, processing pathways 421-423 may each include any suitable number of convolution layers (e.g., 424-426) to extract feature data ($F_1$, $F_2$, $F_3$) at different resolution levels from image data 411. In practice, each convolution layer may be configured to extract feature data (e.g., 2D or 3D feature map) at a particular resolution level by applying filter(s) or kernel(s) to overlapping regions of its input. Numerical values of parameters in the convolution filters are learned during training phase 401. For example, the convolution layer may create a 2D feature map that includes features that appear in 2D image data, or a 3D feature map for 3D image data. This automatic feature extraction approach should be distinguished from conventional approaches that rely on hand-designed features.

Deep learning engine 400 further includes additional convolution layers or blocks 450-470 and mixing blocks 480 (one shown for simplicity) to combine feature data ($F_1$, $F_2$, $F_3$) from processing pathways 421-423 in a staged manner. In particular, third feature data ($F_3$) from third processing pathway 423 may be upsampled from the lowest resolution level $R_3$ to the intermediate resolution level $R_2$ using upsampling block 441. The upsampled third feature data ($F_3$) is then combined with second feature data ($F_2$) from second processing pathway 422 using convolutional block 450, thereby generating first combined set ($C_1$). As an optimization strategy, convolutional block 450 may be configured to "smooth" or "refine" the second feature data ($F_2$) and upsampled third feature data ($F_3$) before another stage of upsampling (e.g., 2×) is performed using subsequent upsampling blocks 442-443.

The feature data ($F_1$, $F_2$, $F_3$) from all processing pathways 421-423 are then combined using additional convolutional blocks 460-470, thereby generating second combined set ($C_2$). In particular, the feature data may be combined by upsampling a lower resolution path to the resolution of a higher resolution path. To bring different feature data to the same resolution level, upsampling blocks 442-443 may be used to upsample first combined set ($C_1$) from convolutional block 450. In practice, convolutional blocks included in processing pathways 421-423, as well as convolutional blocks 450-470 may be of any suitable configuration (e.g., 3×3×3 convolutions).

Second combined set ($C_2$) generated using convolutional blocks 460-470 is then processed using mixing block 480 to produce output data=estimated structure data 482. Mixing block(s) 480 is configured to massage (e.g., via 1×1×1 convolutions) the final set of features into the final segmentation decision (i.e., estimated structure data 482). Estimated structure data 482 may specify such as voxel-based classification data associated with a treatment volume identified from image data 411. For example, a voxel may be classified as a target (e.g., label="TAR") or an OAR (e.g., label="OAR"). In practice, label="OAR" may represent a larger group of labels, such as "Rectum," "Bladder," "Brainstem," or any other anatomically-defined volume. Further, label="TAR" may represent a tumor or treatment volume.

The above training steps may be repeated during training phase 401 to minimize the error between the expected result in training structure data 412 and estimated structure data 482. Depending on the desired implementation, deep learning engine 400 may be implemented using any suitable convolutional neural network architecture(s), such as U-net, LeNet, AlexNet, ResNet, V-net, DenseNet, etc. For example, the U-net architecture includes a contracting path (left side) and an expansive path (right side). The contracting path includes repeated application of convolutions, followed by a rectified linear unit (ReLU) and max polling operation(s). Each step in the expansive path may include upsampling of the feature map followed by convolutions, etc. It should be noted that processing pathways 421-423 may use the same architecture, or different ones.

(c) Inference Phase

Once trained, deep learning engine 400 may be used by a clinician during inference phase 402 to perform segmentation to generate output data=patient structure data 260/492 based on input data=image data 210/491 of a particular patient. Image data 210/491 may be processed by processing pathways 421-423 of deep learning engine 400 at respective resolution levels to enlarge the receptive field. The example process (see blocks 310-370) explained using FIG. 3 may be applied to perform automatic segmentation, and will not be repeated here for brevity.

Dose Prediction

Figure 5:
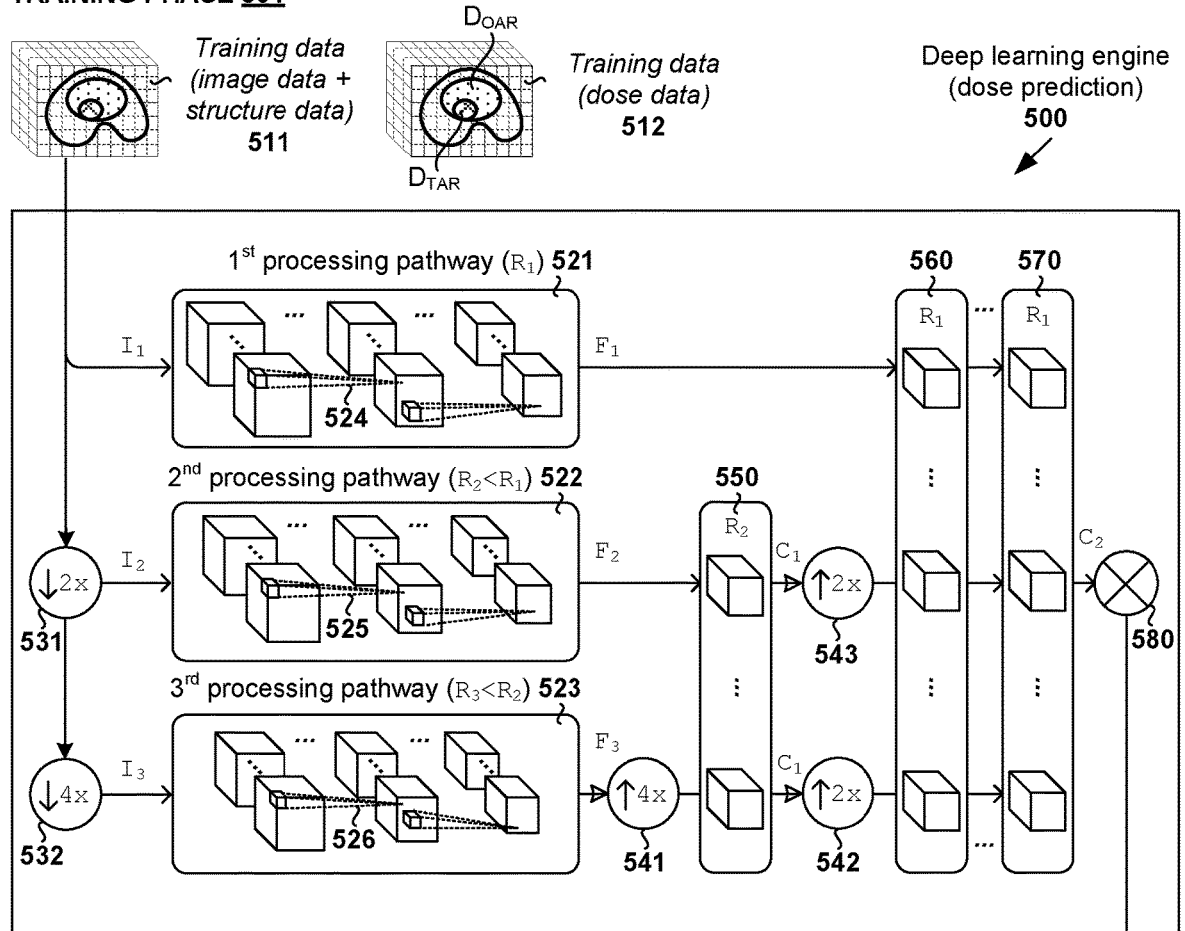
FIG. 5 is a schematic diagram illustrating an example deep learning engine to perform dose prediction for radiotherapy treatment planning.
Figure 5:
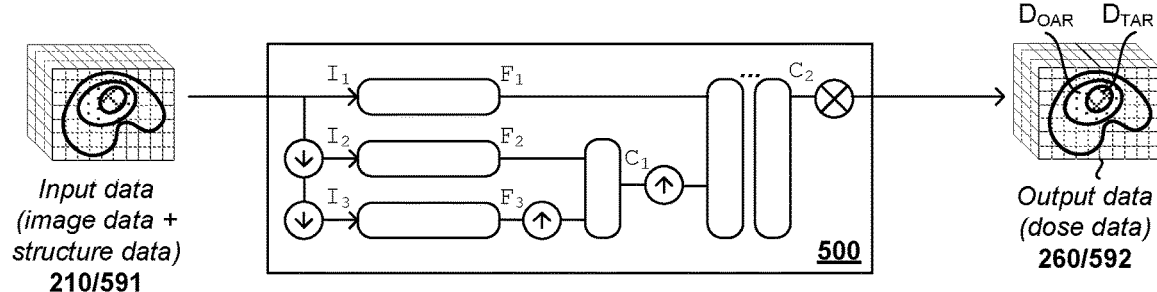

FIG. 5 is a schematic diagram illustrating example deep learning engine 500 to perform dose prediction for radiotherapy treatment planning. Similar to the example in FIG. 4, deep learning engine 500 includes K=3 processing pathways (see 521-523) that are trained during training phase 501. Once trained, deep learning engine 500 may be used (e.g., by a clinician) to perform dose prediction for actual patients during inference phase 502.

(a) Training Data

During training phase 501, deep learning engine 500 may be trained using any suitable training data 511-512 relating to dose prediction. In practice, training data 511-512 may include example input data=image data and structure data 511 (i.e., segmented image data), and example output data=dose data 512. Dose data 512 (e.g., 3D dose data) may specify dose distributions for a target (denoted "$D_{TAR}$") and an OAR (denoted "$D_{OAR}$"). In practice (not shown in FIG. 5 for simplicity), dose data 512 may specify the dose distributions for the whole 3D volume, not just the target and OAR volumes. Depending on the desired implementation, dose data 512 may include spatial biological effect data (e.g., fractionation corrected dose) and/or cover only part of the treatment volume.

For example, in relation to prostate cancer, dose data 512 may specify dose distributions for a target representing the patient's prostate, and an OAR representing a proximal healthy structure such as rectum or bladder. In relation to lung cancer treatment, dose data 512 may specify dose distributions for a target representing cancerous lung tissue, and an OAR representing proximal healthy lung tissue, esophagus, heart, etc. In relation to brain cancer, dose data 512 may specify dose distributions for a target representing a brain tumor, and an OAR representing a proximal optic nerve, brain stem, etc.

The aim of training phase 501 is to train deep learning engine 500 to perform dose prediction by mapping input data=image data and corresponding structure data 511 to example output data=dose data 512. Training phase 501 may involve finding weights (e.g., kernel parameters) that minimize the training error between training dose data 512, and estimated dose data 582 generated by deep learning engine 500. Any suitable constraint(s) may be used, such as limiting dose prediction to the vicinity of target(s) or certain dose levels only.

(b) Processing Pathways and Layers

Similar to the example in FIG. 4, deep learning engine 500 in FIG. 5 includes three processing pathways 521-523 (k=1, 2, 3) to process image data at different resolution levels ($R_k=R_1, R_2, R_3$). First processing pathway 521 (k=1) is configured to process first image data ($i_1$) at a first resolution level $R_1$ (e.g., 1×). Second processing pathway 522 (k=2) is configured to process second image data ($I_2$) at a second resolution level $R_2<R_1$ to enlarge the receptive field. Third processing pathway 523 (k=3) is configured to process third image data ($I_3$) at a third resolution level $R_3<R_2<R_1$ to further enlarge the receptive field.

In the example in FIG. 5, the input to first processing pathway 521 is image data 511. The input to second processing pathway 522 is image data ($I_2$) that has been downsampled (e.g., by a factor of 2×) by downsampling block 531. The input to the third processing pathway 523 is image data ($I_3$) that has been downsampled by both downsampling blocks 531-532 (e.g., by a total factor of 6×). Downsampling blocks 531-532 have matching upsampling blocks 541-543 for upsampling before feature data (see $F_1$, $F_2$, $F_3$) from respective processing pathways 521-523 are combined.

Deep learning engine 500 further includes additional convolution layers or blocks 550-570 and mixing blocks 580 (one shown for simplicity) to combine feature data ($F_1$, $F_2$, $F_3$) from processing pathways 521-523 in stages. Similarly, third feature data ($F_3$) may be upsampled using upsampling block 541 (e.g., by a factor of 4×) before being combined with second feature data ($F_2$) using convolutional block 550, thereby generating first combined set ($C_1$). Further, first combined set ($C_1$) may be upsampled using upsampling blocks 542-543 (e.g., by a factor of 2×) before being combined with first feature data ($F_1$) using convolutional blocks 560-570, thereby generating second combined set ($C_2$). Mixing block(s) 580 is configured to massage (e.g., using 1×1×1 convolutions) the final set of features into the final dose prediction decision (i.e., estimated dose data 582).

(c) Inference Phase

Once trained, deep learning engine 500 may be used by a clinician during inference phase 502 to perform dose prediction to generate output data=dose data 260/592 based on input data=image data 210/591 of a particular patient. Image data 210/591 may be processed by processing pathways 521-523 of deep learning engine 500 at respective resolution levels to enlarge the receptive field. The example process (see blocks 310-370) explained using FIG. 3 may be applied to perform dose prediction, and will not be repeated here for brevity.

(d) Variations

In practice, deep learning engine 200/400/500 may be trained to process data relating to any suitable number of resolution levels. In practice, the number of processing pathways and corresponding resolution levels may depend on the input image data. For example, at some point, downsampling may not reveal additional features of interest because the data would be too coarse. Medical image data resolution tends to be quite high, and three or more resolution levels may be appropriate to achieve efficiency gains.

In the case of K=4, a fourth processing pathway may be used to process fourth image data ($I_4$) associated with a fourth resolution level. For example, the fourth image data ($I_4$) may be generated by downsampling the first image data ($I_1$), second image data ($I_2$) or third image data ($I_3$) using any suitable downsampling factor. Feature data ($F_1$, $F_2$, $F_3$, $F_4$) from respective K=4 processing pathways may be combined in staged manner to improve efficiency. For example, $F_4$ and $F_3$ may be combined first, followed by $F_2$, and finally $F_1$ (e.g., in the order of $F_K$, $F_1$).

Besides automatic segmentation in FIG. 4 and dose prediction in FIG. 5, examples of the present disclosure may be implemented to perform treatment delivery data prediction. In this case, the treatment delivery data (i.e., output data) may include structure projection data, fluence map data, etc. For example, deep learning engine 200 may be trained to perform structure projection data, such as based on image data, structure data, dose data, or any combination thereof. The structure projection data may include data relating to beam orientations and machine trajectories for a treatment delivery system (see 160 in FIG. 1). In another example, deep learning engine 200 may be trained to perform fluence map estimation, such as 2D fluence maps for a set of beam orientations/trajectories, machine control point data (e.g., jaw and leaf positions, gantry and couch positions), etc. Fluence maps will be explained further using FIG. 9.

Input data and output data of deep learning engine 200/400/500 may include any suitable additional and/or alternative data. For example, field geometry data could be input or outputs for all applications. Other examples include monitor units (amount of radiation counted by machine), quality of plan estimate (acceptable or not), daily dose prescription (output), field size or other machine parameters, couch positions parameters or isocenter position within patient, treatment strategy (use movement control mechanism or not, boost or no boost), treat or no treat decision.

Adaptive Radiotherapy (ART)

In radiotherapy, the treatment goal is to be able to deliver a high dose to the target (e.g., to kill cancer cells) while sparing the healthy tissue (e.g., to minimize adverse effect on critical OARs). As such, it is important to deliver to the correct spot during the span of the radiotherapy treatment. However, the situation or condition of a patient's anatomy at the time of delivery might differ considerably from that considered in a treatment plan. For example, the shape, size and position of critical organs might have changed compared to those in the planning image data (e.g., CT images). The difference might be caused by various factors, such as internal organ movement (e.g., bladder filing, bowel movement), patient's weight loss, tumor shrinkage or expansion, etc. In certain cases, the existing treatment plan that is generated based on the planning image data may no longer satisfy the goal of the treatment, and a new treatment plan is required. This is known as ART.

For example, CT image data is usually acquired during a planning phase (i.e., prior to a treatment phase) for the purpose of treatment planning. A treatment plan may be generated based on manual segmentation of the CT image data. During the treatment phase (e.g., near or at the time of treatment delivery), CBCT image data may be acquired to monitor any changes in the patient's condition. A clinician may compare the CBCT image data with the CT image data to assess whether the treatment plan is still applicable to produce precise dose delivery. If the treatment plan is no longer satisfying the treatment goal, the treatment plan needs to be adjusted.

Conventionally, ART generally involves the clinician repeating the manual segmentation step on the newly acquired CBCT image data to improve the quality of the treatment plan. Depending on the case and/or treatment area, segmentation is easily one of the costliest bottlenecks in ART because the number of structures and the complexity of their shapes may vary. For example, contouring may take from few minutes to few hours. In some cases, the patient may not be treated in a timely manner because re-scan may be required to continue the planning process offline. The patient cannot continue the treatment until the new plan is ready, which has the undesirable effect of delaying treatment.

According to examples of the present disclosure, ART planning may be improved using deep learning engines. In the following, two example approaches will be explained. The first approach according to FIG. 6 and FIG. 7 may be implemented when the CBCT image data ("treatment image data") acquired during a treatment phase is significantly different from the CT image data ("planning image data") acquired prior to the treatment phase. Otherwise, the second approach according to FIG. 6 and FIG. 7 may be implemented.

Figure 6:
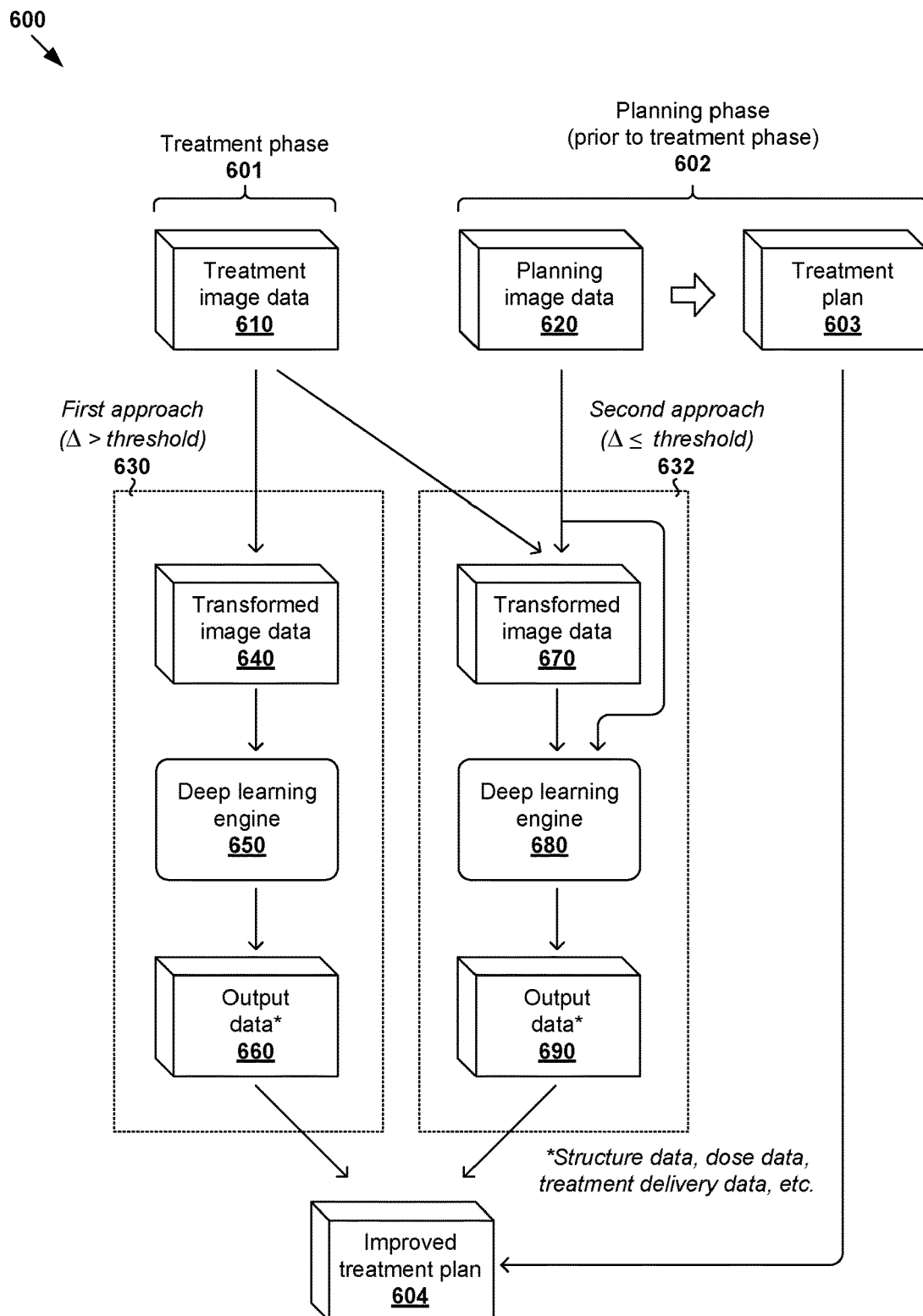
FIG. 6 is schematic diagram illustrating an example process flow for a computer system to perform adaptive radiotherapy treatment (ART) planning using a deep learning engine.

In more detail, FIG. 6 is a schematic diagram illustrating example process flow 600 for a computer system to perform adaptive radiotherapy treatment planning using a deep learning engine. Example process 600 may include one or more operations, functions, or actions illustrated by one or more blocks. The various blocks may be combined into fewer blocks, divided into additional blocks, and/or eliminated based upon the desired implementation. Examples of the present disclosure may be implemented using any suitable computer system, an example of which will be discussed using FIG. 10.

At 610 and 620 in FIG. 6, treatment image data associated with a first imaging modality (e.g., CBCT image data), and planning image data associated with a second imaging modality (e.g., CT image data) may be obtained. Here, the term "obtain" may refer to a computer system accessing or retrieving image data from any suitable source (e.g., another computer system, local memory/storage, remote memory/storage, etc.). The term "treatment image data" may refer generally to any suitable image data that may be acquired during treatment phase 601 (e.g., close to, or on, the day of a scheduled treatment) to determine whether ART is required. The term "planning image data" may refer generally to any suitable image data that may be acquired during planning phase 602 (i.e., prior to the treatment phase 601) for the purpose of generating a treatment plan (see 603) for the patient.

Next, treatment image data 610 and planning image data 620 may be compared to determine whether an update of the treatment plan generated based on the planning image data is required. If yes (i.e., update required), either a first approach (see 640-660) or a second approach (see 670-690) may be implemented based on whether their difference exceeds a significance threshold. In particular, at 630 in FIG. 3, the first approach may be implemented in response to determination that a difference between treatment image data 610 and planning image data 620 exceeds a predetermined significance threshold. Otherwise, at 632 in FIG. 6, in response to determination that their difference does not exceed the predetermined significance threshold, the second approach may be implemented. If the patient's condition has changed significantly since the planning phase 602, the first approach may be implemented based on treatment image data 610. If the difference is less significant, the second approach may be implemented to take advantage of the information in both treatment image data 610 and planning image data 620.

The selection between the first approach and the second approach may be performed manually (e.g., by a clinician) or programmatically (e.g., by a computer system). The "predetermined significance threshold" may be associated with (e.g., set based on, relating to) at least one of the following: shape, size or position change of a target requiring dose delivery; and shape, size or position change of healthy tissue (e.g., OAR) proximal to the target. Depending on the relevant clinical expertise, any suitable quality metric data may be used to assess distance or error mapping between treatment image data 610 and planning image data 620, such as target size, shift in tumor position (e.g., the position of voxels associated with the target in 3D mapping), distance from target to OARs (e.g., distance to surface or centroid), dosimetric values in target and OARs if the original field setup is used in the new situation, etc.

Figure 7:
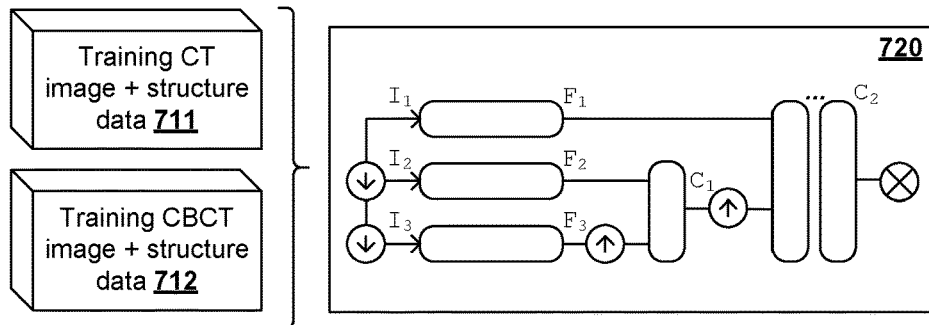
FIG. 7 is a schematic diagram illustrating a first example approach for ART planning according to the example in FIG. 6.
Figure 7:
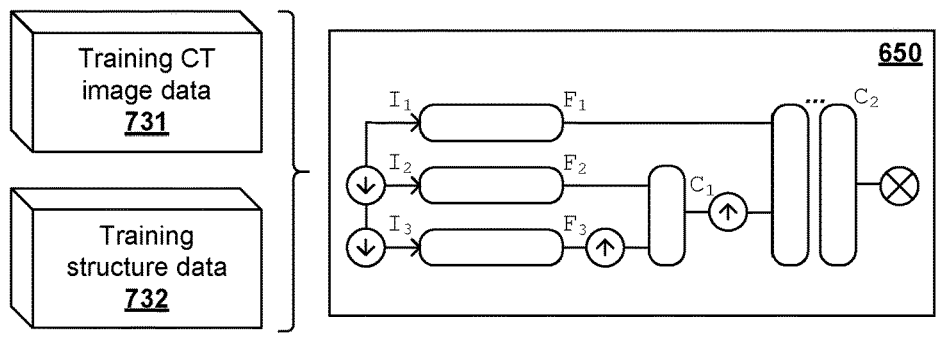
Figure 7:
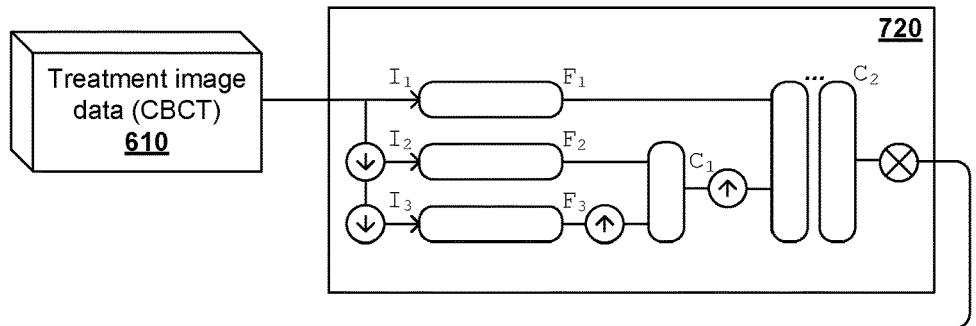
Figure 7:
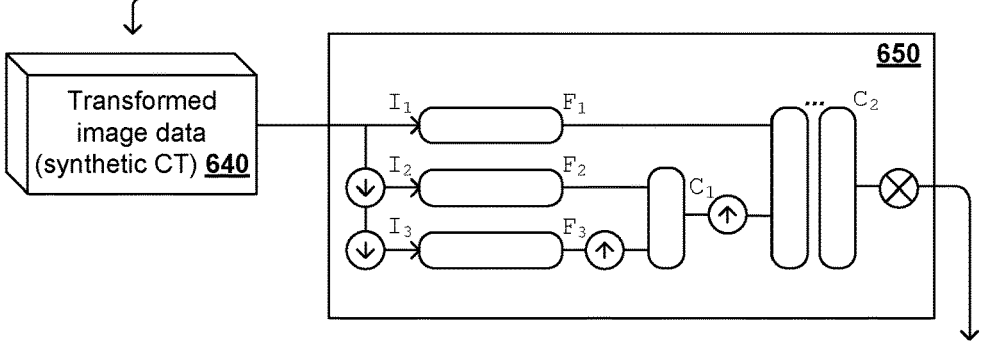
Figure 8:
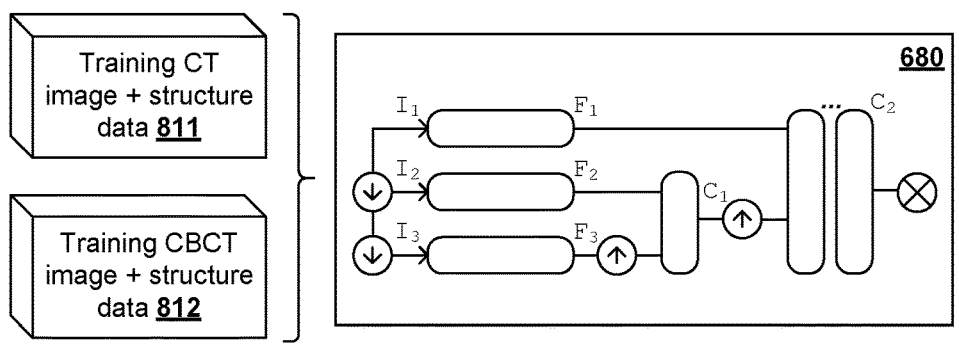
FIG. 8 is a schematic diagram illustrating a second example approach for ART planning according to the example in FIG. 6.
Figure 8:
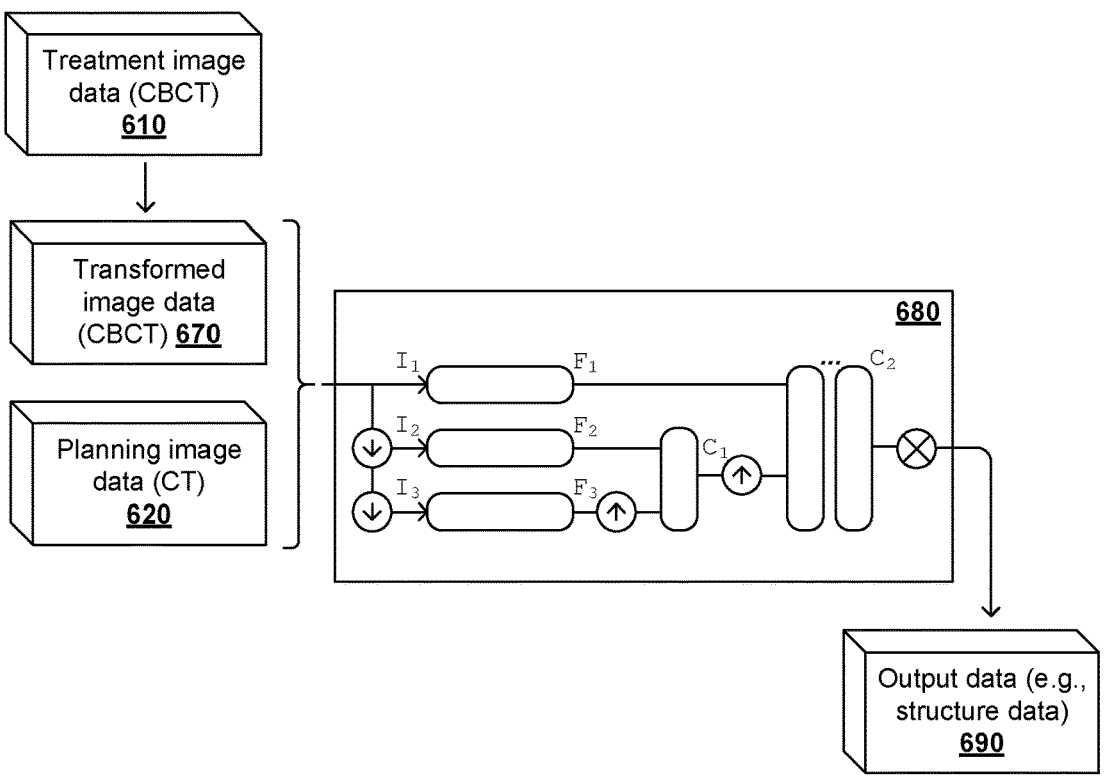

It should be understood that the examples in FIG. 6 to FIG. 8 are applicable to image data acquired any suitable imaging modality or modalities (i.e., not limited to CT and CBCT image data). For example, treatment image data 610 may be in the form of CBCT image data, and planning image data 620 in the form of CT image data, ultrasound image data, MRI image data, PET image data, SPECT or camera image data (e.g., using a time of flight camera to capture the patient's body outline), etc. In practice, there are generally limited options to acquire treatment image data 610 given the limited capabilities of the treatment delivery machine. For example, CBCT image data acquired during treatment has a relatively degraded image quality compared to CT image data acquired for treatment planning purposes. The area of the patient's anatomy scanned by a CBCT is generally smaller than the area of the CT, thus some structures might not be fully visible in the CBCT image data.

In the case of treatment image data 610=CT image data (e.g., associated with one energy level), planning image data 620 may be in the form of CT image data associated with a different energy level, ultrasound image data, MRI image data, PET image data, SPECT image data or camera image data. In the case of treatment image data 610=MRI image data, planning image data 620 may be in the form of CT image data, CBCT image data, ultrasound image data, MRI image data, PET image data, SPECT image data or camera image data. In the case of treatment image data 610=ultrasound image data, planning image data 620 may be in the form of CT image data, CBCT image data, PET image data, MRI image data, SPECT image data or camera image data. In the case of treatment image data 610=PET image data, planning image data 620 may be in the form of CT image data, CBCT image data, ultrasound image data, MRI image data, SPECT image data or camera image data. Alternative and/or additional image data associated with any suitable imaging modality or modalities may be used.

Further, it should be understood that deep learning engine 650/680 in the examples in FIG. 6 to FIG. 8 may be implemented using any suitable deep learning technique(s). In the following, the deep learning architecture with multiple processing pathways in FIG. 1 to FIG. 5 will be used as an example. Depending on the desired implementation, any alternative and/or additional deep learning model(s) may be used (i.e., single or multiple processing pathways). Examples of the present disclosure may be implemented to improve the efficiency of ART, which may improve customer satisfaction, increase the number of patients that can be treated and maintain a set level of planning quality for patients. In the following, CBCT image data will be used as an example "treatment image data associated with a first imaging modality" and CT image as example "treatment image data associated with a second imaging modality."

(a) First Approach (Difference>Significance Threshold)

In the example in FIG. 6, the first example approach may be performed in response to determination that an update of a treatment plan generated based on planning image data 620 is required, and the difference between treatment image data 610 and planning image data 620 exceeds a predetermined significance threshold. Since there is a significant deviation, it is not necessary to rely on planning image data 620 during ART to avoid any adverse effect on the treatment delivery.

In particular, at 640 in FIG. 6, treatment image data 610 (e.g., CBCT image data) may be transformed to generate transformed image data associated with the second imaging modality (e.g., synthetic CT image data). At 650 in FIG. 6, transformed image data 640 may be processed using a deep learning engine to generate any suitable output data for updating treatment plan 603. The output data may be patient structure data (e.g., identifying one or more targets and/or OARs, etc.) associated with the patient, dose data associated with the patient (e.g., dose distributions for one or more targets and/or OARs), treatment delivery data (e.g., beam orientations and/or trajectories, machine control point data, fluence maps, etc.) associated with a treatment delivery system, or any combination thereof.

Example implementation of the first approach according to blocks 640-660 in FIG. 6 will be explained using FIG. 7, which is a schematic diagram illustrating first example approach 700 FIG. 7 for ART planning according to the example in FIG. 6. Example process 700 may include one or more operations, functions, or actions illustrated by one or more blocks. The various blocks may be combined into fewer blocks, divided into additional blocks, and/or eliminated based upon the desired implementation. Example process 700 may be implemented using any suitable computer system, an example of which will be discussed using FIG. 10.

During training phase 701, deep learning engine 650 may be trained to generate output data 660 using any suitable training data, such as training CT image data (see 731) and corresponding output data. In the case of automatic segmentation, training structure data 732 for CT image data 731 may be used. Alternatively (not shown in FIG. 7 for simplicity), deep learning engine 650 may be trained to perform generate structure data 732, dose prediction to generate dose data, treatment delivery data estimation to generate treatment delivery data, or any combination thereof. Using the examples in FIG. 2 and FIG. 3, deep learning engine 650 may include multiple processing pathways to process image data ($I_1$, $I_2$, $I_3$) at different resolution levels ($R_1$, $R_2$, $R_3$). The examples discussed using FIG. 1 to FIG. 5 are also applicable here and will not be repeated for brevity. Using deep learning engine 650 instead of manual approaches, the efficiency of ART may be improved.

In the example in FIG. 7, transformed image data 640 may be generated using deep learning engine 720 that is trained to map image data associated with one imaging modality (e.g., CBCT) to another imaging modality (e.g., CT). For example in FIG. 7, deep learning engine 720 may be trained to map CBCT image data to CT image data. In one example, deep learning engine 720 may be trained using training data that includes CT image data and corresponding structure data (see 711), as well as CBCT image data and corresponding structure data (see 712). The examples discussed using FIG. 1 to FIG. 5 are also applicable here and will not be repeated for brevity. Alternatively, algorithmic approaches may be used instead of deep learning engine 720, such as rigid or deformable registration algorithms, etc.

During inference phase 702, treatment planning data 610 (e.g., CBCT image data) may be processed using trained deep learning engine 720 to generate transformed image data 640 (e.g., synthetic CT image data). Next, transformed image data 640 may be processed using deep learning engine 650 to generate output data 660. For example in FIG. 7, deep learning engine 650 may be trained to perform automatic segmentation to generate output=structure data identifying target(s) and OAR(s) associated with the patient. Alternatively, deep learning engine 650 may be trained to perform dose prediction, projection data estimation, etc. Output data 660 may then be used to update treatment plan 603 to reflect changes in the patient's condition, thereby improving treatment delivery quality. Treatment may then be delivered based on improved treatment plan 604 in FIG. 6.

(b) Second Approach (Difference≤Significance Threshold)

Referring to FIG. 6 again, the second example approach may be performed in response to determination that an update of a treatment plan generated based on planning image data 620 is required, and the difference between treatment image data 610 and planning image data 620 does not exceed a predetermined significance threshold. Since the difference is less significant, ART benefits from two sets of image data, i.e., both treatment image data 610 and planning image data 620. This is because, for example, CT image data may include additional data because it does not suffer from severe artifacts compared to CBCT image data.

In more detail, at 680 and 690 in FIG. 6, treatment image data 610 and planning image data 620 may be processed using a deep learning engine to generate any suitable output data for updating treatment plan 603. Similarly, output data 690 may include patient structure data (e.g., identifying one or more targets and OARs, etc.) associated with the patient, dose data associated with the patient (e.g., dose distributions for one or more targets and OARs), treatment delivery data (e.g., beam orientations and/or trajectories, machine control point data, fluence map data, etc.) associated with a treatment delivery system, or any combination thereof.

Prior to the processing using deep learning engine 680, treatment image data 610 may be transformed to generate transformed image data (see 670), such as by performing image registration to register treatment image data 610 against planning image data 620, etc. Any suitable approach for image registration may be used, such as algorithmic approach, machine learning approach, deep learning approach, etc. Image registration may be performed to obtain a correspondence between treatment image data 610 and planning image data 620.

For example, after CBCT image data has been deformed to match CT image data, they may be fed into deep learning engine 680 to generate output data 690. In practice, image registration may be performed using any suitable approach, such as deep learning approach, algorithms, etc. One example deep learning approach for image registration is disclosed in a paper entitled "Quicksilver: Fast Predictive Image Registration—a Deep Learning Approach" (2017) authored by Xiao, Y., Kwitt, R., Styner, M., Niethammer, M., and published in NeuroImage (vol. 158, 2017, pages 378-396). Such approach may be implemented to perform deformable image registration using patch-wise prediction of a deformation model based on image appearance. A deep encoder-decoder network may be used as the prediction model.

It should be noted that transformed image data 670 in the second approach is generated based on both treatment image data 610 and planning image data 620 (i.e., two inputs, such as CT and CBCT image data). This should be contrasted against the first approach, in which transformed image data 640 is generated based on one input=treatment image data 610 (e.g., CBCT image data of the day). Both approaches may rely on image registration for the transformation.

Example implementation of the second approach according to blocks 670-690 in FIG. 6 will be explained using FIG. 8, which is a schematic diagram illustrating second example approach 800 FIG. 8 for ART planning according to the example in FIG. 6. Example process 800 may include one or more operations, functions, or actions illustrated by one or more blocks. The various blocks may be combined into fewer blocks, divided into additional blocks, and/or eliminated based upon the desired implementation. Example process 800 may be implemented using any suitable computer system, an example of which will be discussed using FIG. 10.

During training phase 801, deep learning engine 680 may be trained to generate output data 690 using any suitable training data, such as training CT image and structure data 811, as well as training CBCT image and structure data 812. The aim is to train deep learning engine 680 to generate output data (e.g., structure data in the case of automatic segmentation) based on two sets of image data acquired using different imaging modalities, such as CT and CBCT in FIG. 8.

Deep learning engine 680 may be implemented using any suitable deep learning model. Using the examples in FIG. 1 to FIG. 5, deep learning engine 680 may include multiple processing pathways to process both sets of CT and CBCT image data ($I_1$, $I_2$, $I_3$) at different resolution levels ($R_1$, $R_2$, $R_3$). Compared to using a single set of image data, the input image data to deep learning engine 680 may have two values representing the CT and CBCT image data respectively. Convolutional layers in deep learning engine 680 may be configured to transform the input image data into more or less abstract features by combining data from all modalities. Additional implementation details discussed using FIG. 1 to FIG. 5 are also applicable here and will not be repeated for brevity.

During inference phase 802, trained deep learning engine 680 to process two sets of image data, i.e., planning image data 620 and transformed image data 670 generated using image registration, etc. In the case of automatic segmentation, output data 690 may include structure data identifying target(s) and OAR(s) associated with the patient. Alternatively, deep learning engine 680 may be trained to perform dose prediction, treatment delivery data estimation, etc. Output data 690 may then be used to update treatment plan 603 to reflect changes in the patient's condition, thereby improving treatment delivery quality. Treatment may then be delivered based on improved treatment plan 604 in FIG. 6.

Using multiple sets of image data acquired using different imaging modalities, improved output data (e.g., better quality contours) may be produced than having just one set of image data. Compared to the first approach, the two different imaging technologies generally provide more information compared to one imaging technology. For example, time of flight camera system provides information about patient surface from a large area but not information from inside patient, while CBCT provides information from inside patient but for a limited field of view, time of flight camera system capturing movement and CBCT. These two sets of image data may be interpreted by deep neural network technology to provide information in one agreed format (for example CT image, CT image and segmentation, segmentations, 3D density map, 3d density map with movements, segmentations with movements, etc.).

Example Treatment Plan

Figure 9:
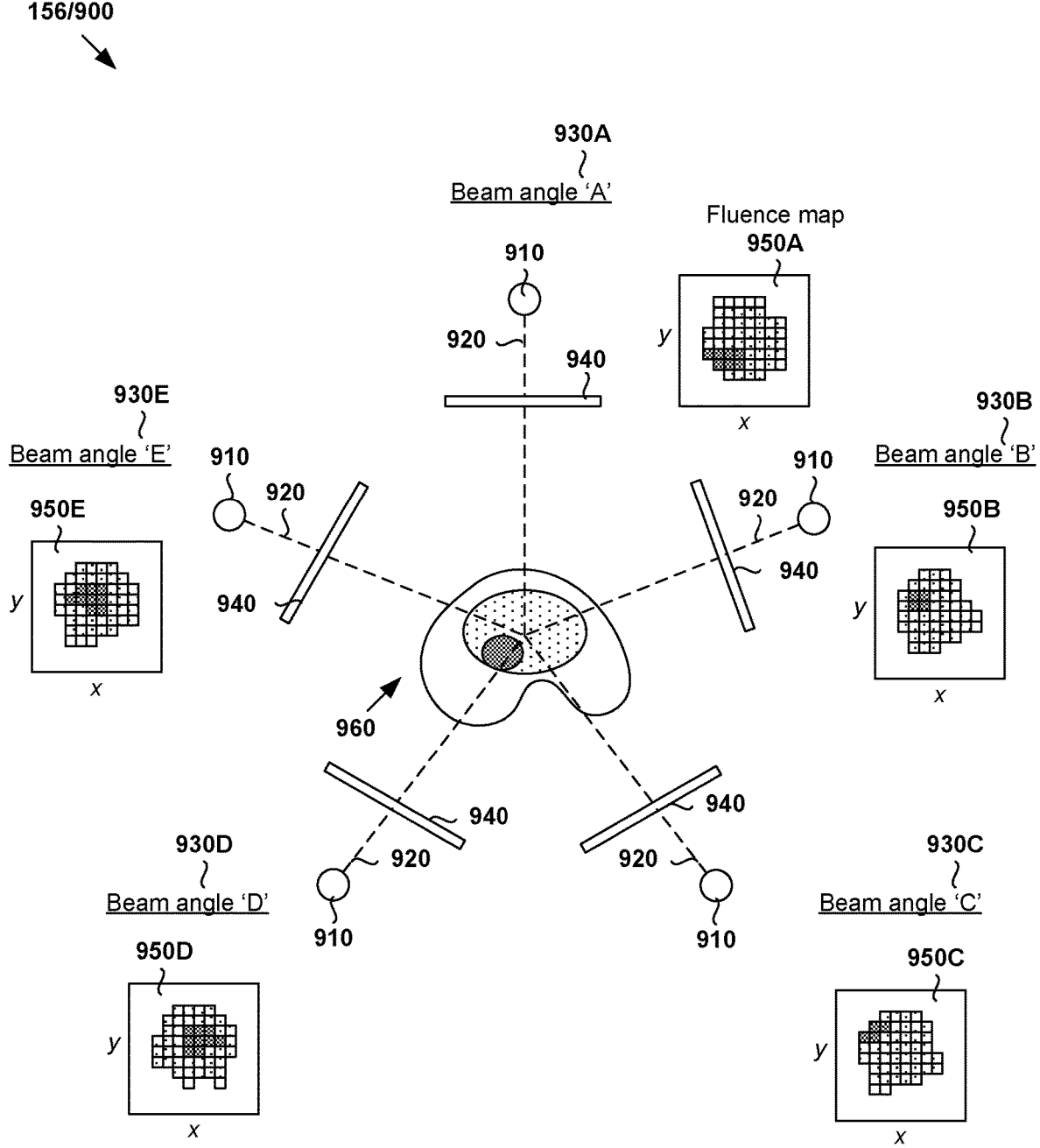
FIG. 9 is schematic diagram illustrating an example treatment plan generated or improved based on output data in the examples in FIG. 1 to FIG. 8.
Figure 10:
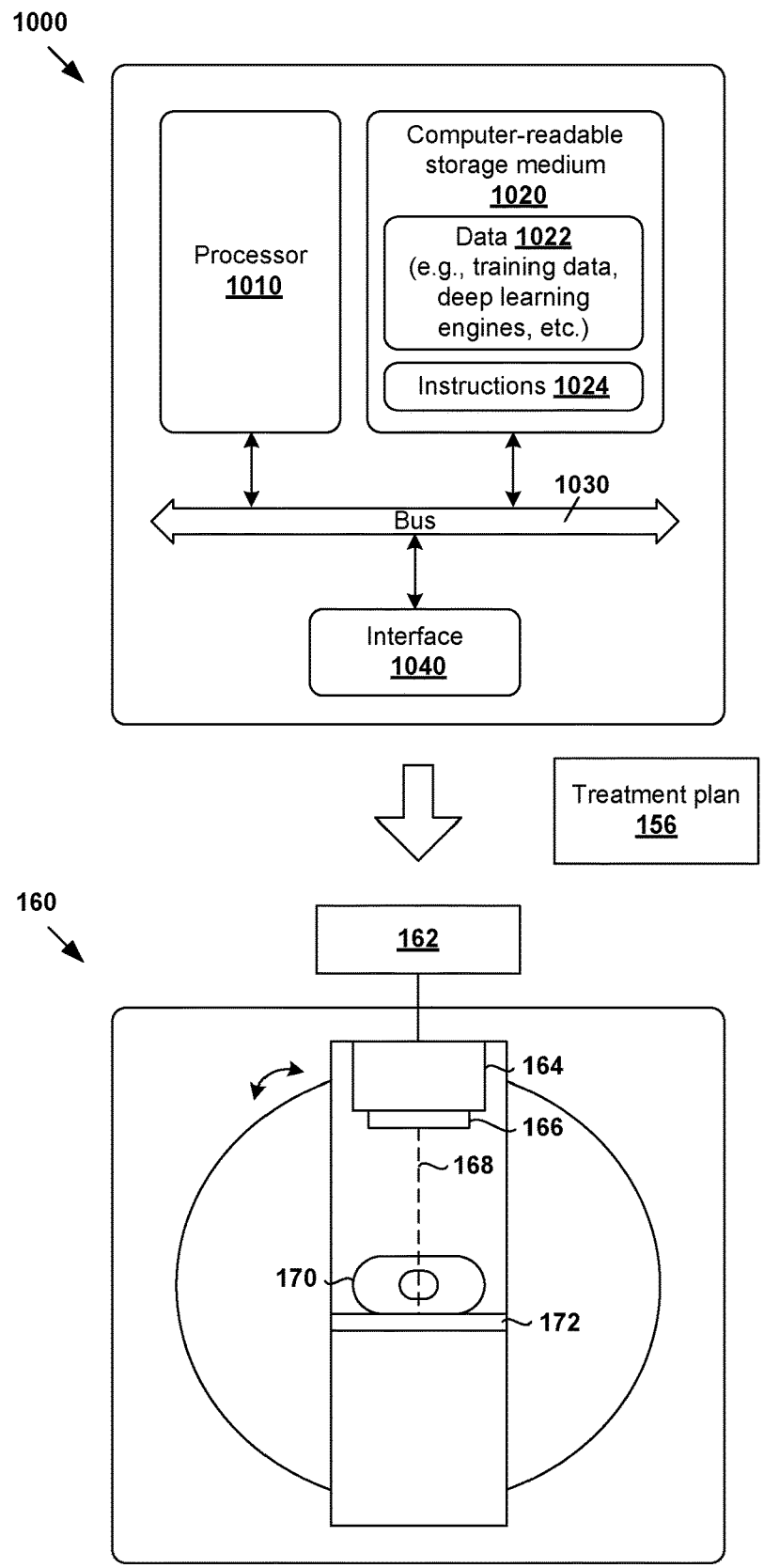
FIG. 10 is a schematic diagram of an example computer system to perform radiotherapy treatment planning and/or adaptive radiotherapy treatment planning.

FIG. 9 is a schematic diagram of example treatment plan 156/900 generated or improved based on output data in the examples in FIG. 1 to FIG. 8. Treatment plan 156 may be delivered using any suitable treatment delivery system that includes radiation source 910 to project radiation beam 920 onto treatment volume 960 representing the patient's anatomy at various beam angles 930. Although not shown in FIG. 9 for simplicity, radiation source 910 may include a linear accelerator to accelerate radiation beam 920 and a collimator (e.g., MLC) to modify or modulate radiation beam 920. In another example, radiation beam 920 may be modulated by scanning it across a target patient in a specific pattern with various energies and dwell times (e.g., as in proton therapy). A controller (e.g., computer system) may be used to control the operation of radiation source 920 according to treatment plan 156.

During treatment delivery, radiation source 910 may be rotatable using a gantry around a patient, or the patient may be rotated (as in some proton radiotherapy solutions) to emit radiation beam 920 at various beam orientations or angles relative to the patient. For example, five equally-spaced beam angles 930A-E (also labelled "A," "B," "C," "D" and "E") may be selected using a deep learning engine configured to perform treatment delivery data estimation. In practice, any suitable number of beam and/or table or chair angles 930 (e.g., five, seven, etc.) may be selected. At each beam angle, radiation beam 920 is associated with fluence plane 940 (also known as an intersection plane) situated outside the patient envelope along a beam axis extending from radiation source 910 to treatment volume 960. As shown in FIG. 9, fluence plane 940 is generally at a known distance from the isocenter.

During radiotherapy treatment planning, treatment plan 156/900 may be generated based on output data 260/492/592 generated using deep learning engine 200/400/500 in the examples in FIG. 1 to FIG. 5. During ART planning, treatment plan 156/900 may be improved based on output data 660/690 generated using deep learning engine 650/680 in the examples in FIG. 6 to FIG. 8.

Computer System

The above examples can be implemented by hardware, software or firmware or a combination thereof. FIG. 10 is a schematic diagram of example computer system 1000 for radiotherapy treatment planning and/or ART planning. In this example, computer system 1005 (also known as a treatment planning system) may include processor 1010, computer-readable storage medium 1020, interface 1040 to interface with radiotherapy treatment delivery system 160, and bus 1030 that facilitates communication among these illustrated components and other components.

Processor 1010 is to perform processes described herein with reference to FIG. 1 to FIG. 9. Computer-readable storage medium 1020 may store any suitable information 1022, such as information relating to training data, deep learning engines, image data, output data, etc. Computer-readable storage medium 1020 may further store computer-readable instructions 1024 which, in response to execution by processor 1010, cause processor 1010 to perform processes described herein. Treatment may be delivered according to treatment plan 156 using treatment planning system 160 explained using FIG. 1, the description of which will not be repeated here for brevity.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Throughout the present disclosure, the terms "first," "second," "third," etc. do not denote any order of importance, but are rather used to distinguish one element from another.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A method for a computer system to perform adaptive radiotherapy treatment planning using a deep learning engine, wherein the method comprises:

obtaining treatment image data associated with a first imaging modality, wherein the treatment image data is acquired during a treatment phase of a patient, and planning image data associated with a second imaging modality is acquired prior to the treatment phase to generate a treatment plan for the patient; and in response to determination that an update of the treatment plan is required, transforming the treatment image data associated with the first imaging modality to generate transformed image data associated with the second imaging modality; and processing, using the deep learning engine, the transformed image data to generate output data for updating the treatment plan, wherein processing the transformed image data comprises:

processing, using a first processing pathway of the deep learning engine, the transformed image data to generate first feature data associated with a first resolution level;

processing, using a second processing pathway of the deep learning engine, the transformed image data to generate second feature data associated with a second resolution level;

processing, using a third processing pathway of the deep learning engine, the transformed image data to generate third feature data associated with a third resolution level; and generating the output data based on the first feature data, second feature data and third feature data.

2. The method of claim 1, wherein the method further comprises:

based on a comparison between the treatment image data and the planning image data, determining that a difference between the treatment image data and the planning image data exceeds a predetermined significance threshold relating to at least one of the following: shape, size or position change of a target requiring dose delivery; and shape, size or position change of healthy tissue proximal to the target.

3. The method of claim 1, wherein processing the treatment image data comprises:

transforming, using a further deep learning engine, the treatment image data to the transformed image data that includes data suitable for treatment planning.

4. The method of claim 1, wherein processing the treatment image data comprises:

transforming, using an image registration algorithm, the treatment image data to the transformed image data that includes data suitable for treatment planning.

5. The method of claim 1, wherein obtaining the treatment image data comprises one of the following:

obtaining the treatment image data in the form of cone beam computed tomography (CBCT) image data, and the planning image data in the form of computed tomography (CT) image data, ultrasound image data, magnetic resonance imaging (MRI) image data, positron emission tomography (PET) image data or camera image data;

obtaining the treatment image data in the form of CT image data, and the planning image data in the form of CT image data associated with a different energy level, ultrasound image data, MRI image data, PET image data or camera image data;

obtaining the treatment image data in the form of MRI image data, and the planning image data in the form of CT image data, CBCT image data, ultrasound image data, MRI image data, PET image data or camera image data;

obtaining the treatment image data in the form of ultrasound image data, and the planning image data in the form of CT image data, CBCT image data, PET image data, MRI image data or camera image data; and obtaining the treatment image data in the form of PET image data, and the planning image data in the form of CT image data, CBCT image data, ultrasound image data, MRI image data or camera image data.

6. The method of claim 1, wherein the method further comprises:
training the deep learning engine to perform one of the following using training data associated with past patients: automatic segmentation to generate the output data in the form of structure data associated with the patient, dose prediction to generate the output data in the form of dose data associated with the patient, and treatment delivery data estimation to generate the output data in the form of treatment delivery data for a treatment delivery system.

7. A non-transitory computer-readable storage medium that includes a set of instructions which, in response to execution by a processor of a computer system, cause the processor to perform a method of adaptive radiotherapy treatment planning using a deep learning engine, wherein the method comprises:
obtaining treatment image data associated with a first imaging modality, wherein the treatment image data is acquired during a treatment phase of a patient, and planning image data associated with a second imaging modality is acquired prior to the treatment phase to generate a treatment plan for the patient; and
in response to determination that an update of the treatment plan is required,
transforming the treatment image data associated with the first imaging modality to generate transformed image data associated with the second imaging modality; and
processing, using the deep learning engine, the transformed image data to generate output data for updating the treatment plan, wherein processing the transformed image data comprises:
processing, using a first processing pathway of the deep learning engine, the transformed image data to generate first feature data associated with a first resolution level;
processing, using a second processing pathway of the deep learning engine, the transformed image data to generate second feature data associated with a second resolution level;
processing, using a third processing pathway of the deep learning engine, the transformed image data to generate third feature data associated with a third resolution level; and
generating the output data based on the first feature data, second feature data and third feature data.

8. The non-transitory computer-readable storage medium of claim 7, wherein the method further comprises:
based on a comparison between the treatment image data and the planning image data, determining that a difference between the treatment image data and the planning image data exceeds a predetermined significance threshold relating to at least one of the following: shape, size or position change of a target requiring dose delivery; and shape, size or position change of healthy tissue proximal to the target.

9. The non-transitory computer-readable storage medium of claim 7, wherein processing the treatment image data comprises:
transforming, using a further deep learning engine, the treatment image data to the transformed image data that includes data suitable for treatment planning.

10. The non-transitory computer-readable storage medium of claim 7, wherein processing the treatment image data comprises:
transforming, using an image registration algorithm, the treatment image data to the transformed image data that includes data suitable for treatment planning.

11. The non-transitory computer-readable storage medium of claim 7, wherein obtaining the treatment image data comprises one of the following:
obtaining the treatment image data in the form of cone beam computed tomography (CBCT) image data, and the planning image data in the form of computed tomography (CT) image data, ultrasound image data, magnetic resonance imaging (MRI) image data, positron emission tomography (PET) image data or camera image data;
obtaining the treatment image data in the form of CT image data, and the planning image data in the form of CT image data associated with a different energy level, ultrasound image data, MRI image data, PET image data or camera image data;
obtaining the treatment image data in the form of MRI image data, and the planning image data in the form of CT image data, CBCT image data, ultrasound image data, MRI image data, PET image data or camera image data;
obtaining the treatment image data in the form of ultrasound image data, and the planning image data in the form of CT image data, CBCT image data, PET image data, MRI image data or camera image data; and
obtaining the treatment image data in the form of PET image data, and the planning image data in the form of CT image data, CBCT image data, ultrasound image data, MRI image data or camera image data.

12. The non-transitory computer-readable storage medium of claim 7, wherein the method further comprises:
training the deep learning engine to perform one of the following using training data associated with past patients: automatic segmentation to generate the output data in the form of structure data associated with the patient, dose prediction to generate the output data in the form of dose data associated with the patient, and treatment delivery data estimation to generate the output data in the form of treatment delivery data for a treatment delivery system.

13. A computer system configured to perform adaptive radiotherapy treatment planning using a deep learning engine, the computer system comprising: a processor and a non-transitory computer-readable medium having stored thereon instructions that, when executed by the processor, cause the processor to:
obtain treatment image data associated with a first imaging modality, wherein the treatment image data is acquired during a treatment phase of a patient, and planning image data associated with a second imaging modality is acquired prior to the treatment phase to generate a treatment plan for the patient; and
in response to determination that an update of the treatment plan is required,
transform the treatment image data associated with the first imaging modality to generate transformed image data associated with the second imaging modality; and
process, using the deep learning engine, the transformed image data to generate output data for updating the treatment plan, wherein the instructions for processing the transformed image data cause the processor to:
  process, using a first processing pathway of the deep learning engine, the transformed image data to generate first feature data associated with a first resolution level;
  process, using a second processing pathway of the deep learning engine, the transformed image data to generate second feature data associated with a second resolution level;
  process, using a third processing pathway of the deep learning engine, the transformed image data to generate third feature data associated with a third resolution level; and
  generate the output data based on the first feature data, second feature data and third feature data.

14. The computer system of claim 13, wherein the instructions further cause the processor to:
  based on a comparison between the treatment image data and the planning image data, determine that a difference between the treatment image data and the planning image data exceeds a predetermined significance threshold relating to at least one of the following: shape, size or position change of a target requiring dose delivery; and shape, size or position change of healthy tissue proximal to the target.

15. The computer system of claim 13, wherein the instructions for processing the treatment image data cause the processor to:
  transform, using a further deep learning engine, the treatment image data to the transformed image data that includes data suitable for treatment planning.

16. The computer system of claim 13, wherein the instructions for processing the treatment image data cause the processor to:
  transform, using an image registration algorithm, the treatment image data to the transformed image data that includes data suitable for treatment planning.

17. The computer system of claim 13, wherein the instructions for obtaining the treatment image data cause the processor to perform one of the following:
  obtain the treatment image data in the form of cone beam computed tomography (CBCT) image data, and the planning image data in the form of computed tomography (CT) image data, ultrasound image data, magnetic resonance imaging (MRI) image data, positron emission tomography (PET) image data or camera image data;
  obtain the treatment image data in the form of CT image data, and the planning image data in the form of CT image data associated with a different energy level, ultrasound image data, MRI image data, PET image data or camera image data;
  obtain the treatment image data in the form of MRI image data, and the planning image data in the form of CT image data, CBCT image data, ultrasound image data, MRI image data, PET image data or camera image data;
  obtain the treatment image data in the form of ultrasound image data, and the planning image data in the form of CT image data, CBCT image data, PET image data, MRI image data or camera image data; and
  obtain the treatment image data in the form of PET image data, and the planning image data in the form of CT image data, CBCT image data, ultrasound image data, MRI image data or camera image data.

18. The computer system of claim 13, wherein the instructions further cause the processor to:
  train the deep learning engine to perform one of the following using training data associated with past patients: automatic segmentation to generate the output data in the form of structure data associated with the patient, dose prediction to generate the output data in the form of dose data associated with the patient, and treatment delivery data estimation to generate the output data in the form of treatment delivery data for a treatment delivery system.

* * * * *